United States Patent
Jagtap et al.

(10) Patent No.: US 9,522,903 B2
(45) Date of Patent: Dec. 20, 2016

(54) MULTIFUNCTIONAL NITROXIDE DERIVATIVES AND USES THEREOF

(71) Applicant: RADIKAL THERAPEUTICS INC, West Tisbury, MA (US)

(72) Inventors: Prakash Jagtap, North Andover, MA (US); Andrew Lurie Salzman, West Tisbury, MA (US)

(73) Assignee: Radikal Therapeutics Inc., West Tisbury, MA (US)

( * ) Notice: Subject to any disclaimer, the term of this patent is extended or adjusted under 35 U.S.C. 154(b) by 0 days.

(21) Appl. No.: 14/815,783

(22) Filed: Jul. 31, 2015

(65) Prior Publication Data

US 2015/0336932 A1 Nov. 26, 2015

Related U.S. Application Data

(62) Division of application No. 13/992,396, filed as application No. PCT/IL2011/000931 on Dec. 8, 2011, now Pat. No. 9,102,659.

(60) Provisional application No. 61/421,382, filed on Dec. 9, 2010.

(51) Int. Cl.

| C07D 211/46 | (2006.01) |
|---|---|
| C07D 223/12 | (2006.01) |
| C07D 401/12 | (2006.01) |
| C07D 207/46 | (2006.01) |
| C07D 211/94 | (2006.01) |

(52) U.S. Cl.
CPC ........... *C07D 401/12* (2013.01); *C07D 207/46* (2013.01); *C07D 211/94* (2013.01); *C07D 223/12* (2013.01)

(58) Field of Classification Search
CPC ... C07D 207/46; C07D 207/94; C07D 223/12; C07D 401/12
USPC .............. 540/597, 604; 546/193, 246, 278.6
See application file for complete search history.

(56) References Cited

U.S. PATENT DOCUMENTS

| 4,057,636 A | 11/1977 | Petersen |
| 5,011,837 A | 4/1991 | Atwal et al. |
| 8,202,852 B2 | 6/2012 | Zerangue et al. |
| 2006/0025446 A1 | 2/2006 | Sterling et al. |

FOREIGN PATENT DOCUMENTS

WO    04000331 A1    12/2003

OTHER PUBLICATIONS

Liang "Preparation of cynoguanidine . . . " CA117:212341 (1992).*
Stein et al. "Preparation of caprolactams . . . " CA133:164010 (2000).*
Boschi et al. "Nicorandil analog . . . " Bioorg. Med. Chem. vol. 8, 1727-1732 (2000).*
Petersen et al. "Syntesis and hypotensive . . . " J. Mde. Chem. 21(8) 773-781 (1978).
Pietri et al. "PNitrone spein . . . " Eur. J. Biochem 254 p. 256-265 (1998).
Wipf "Bioisosterism" p. 43-64 (2008).
Liang "Preparation of cyanoguanidine . . . " CA117:212341 (1992). Improper Markush, Fed. Registry v.76(27) 7162-7175 and slide 1, 64-67.
Exhibit I, starting material search p. 1 (2014).
Seddon, Kenneth R., "Pseudopolymorph: A Polemic", Crystal Growth & Design, 2004, vol. 4, No. 6, 1087.
International Search Report and Written Opinion dated Apr. 17, 2012 for International Application No. PCT/IL2011/000931.

* cited by examiner

*Primary Examiner* — Celia Chang
(74) *Attorney, Agent, or Firm* — Knobbe Martens Olson & Bear LLP

(57) ABSTRACT

Multifunctional nitroxide derivatives comprising a potassium channel opener and a reactive oxygen species (ROS) degradation catalyst that can act as an anti-oxidant, as well as pharmaceutical compositions comprising them are provided. The multifunctional compounds and pharmaceutical compositions are useful for treatment of diseases, disorders or conditions associated with oxidative stress or endothelial dysfunction.

20 Claims, 7 Drawing Sheets

MULTIFUNCTIONAL NITROXIDE DERIVATIVES AND USES THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

The present invention relates to compounds comprising a potassium channel opener with superoxide ion ($O_2^-$) catalytic degradation properties and to pharmaceutical compositions comprising them. These compounds are useful for treatment, prevention and/or managing of diseases, disorders and conditions associated with oxidative stress or endothelial dysfunction.

2. Description of the Related Art

Openers of the mitochondrial ATP-regulated potassium channel have been shown to provide cytoprotection in experimental models of redox stress induced by ischemia-reperfusion or inflammation. However, the specificity for the mitochondrial rather than the sarcolemmal $K^+$-ATP channel is important to eliminate the risk of systemic hypotension.

Given the demonstrated benefit in these pathological settings of therapeutic administration of either antioxidants or $K^+$-ATP channel openers, a more substantial benefit may accrue from (i) the concomitant removal of reactive oxygen species (ROS) and (ii) stimulation of endogenous mechanisms (via opening $K^+$-ATP channels) to protect against redox stress. This effect would be maximized if both these actions co-localized in space and time. However, such co-localization would be unlikely to occur by the co-administration of two distinct drugs, such as a separate $K^+$-ATP channel opener and an anti-oxidant molecule, because of the unpredictability of their tissue distribution, metabolism, clearance, excretion, and intracellular localization.

SUMMARY OF THE INVENTION

It has been found in accordance with the present invention that administration of a conjugate of a pyridinocyanoguanidine moiety and the 3-amino-2,2,5,5-tetramethylpyrrolidinyloxy, free radical, more particularly, the oxy radical of 2-cyano-1-(1-hydroxy-2,2,5,5-tetramethylpyrrolidin-3-yl)-3-(pyridin-3-yl)guanidine, is highly beneficial in treatment, prevention and/or managing of various diseases, disorders or conditions associated with oxidative stress or endothelial dysfunction such as myocardial ischemia-reperfusion injury and renal ischemia-reperfusion injury, as well as acute chlorine inhalation injury.

In one aspect, the present invention thus relates to a multifunctional nitroxide derivative of the general formula I:

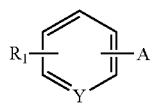

I wherein Y is N, CH or N(→O),
or an enantiomer, diastereomer, racemate, or a pharmaceutically acceptable salt, solvate or prodrug thereof, wherein A is a moiety of the general formula II linked through its terminal —NH group to any carbon atom of the pyridine, phenyl, or pyridine oxide ring:

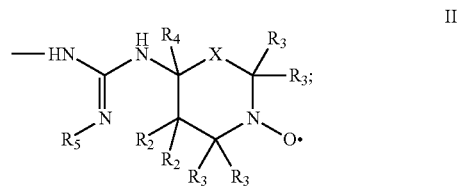

II

X is absent or —$(CR_2R_2)_n$—;

$R_1$ is absent or 1 to 5 substituents each independently selected from halogen, —CN, —OH, —$NO_2$, —$N(R_6)_2$, —$OCF_3$, —$CF_3$, —$OR_6$, —$COR_6$, —$COOR_6$, —$CON(R_6)_2$, —$OCOOR_6$, —$OCON(R_6)_2$, —($C_1$-$C_8$)alkyl, —($C_1$-$C_8$)alkylene-$COOR_6$, —$SR_6$, —$SO_2R_6$, —$SO_2N(R_6)_2$, or —$S(=O)R_6$, wherein said —($C_1$-$C_8$)alkyl and —($C_1$-$C_8$)alkylene-$COOR_6$ may optionally be substituted with —OH, —$OR_3$, —$OCF_3$, —$CF_3$, —$COR_3$, —$COOR_3$, —$OCOOR_3$, —$OCON(R_3)_2$, —($C_1$-$C_8$)alkylene-$COOR_3$, —CN, —$NH_2$, —$NO_2$, —SH, —$SR_3$, —($C_1$-$C_8$)alkyl, —O—($C_1$-$C_8$)alkyl, —$N(R_3)_2$, —$CON(R_3)_2$, —$SO_2R_3$, or —$S(=O)R_3$, or two adjacent $R_1$ groups and the carbon atoms to which they are attached form a 5- or 6-membered carbocyclic or heterocyclic ring, ($C_6$-$C_{10}$)aryl, or 6- to 10-membered heteroaryl;

$R_2$ each independently is selected from H, halogen, —$OCF_3$, —$CF_3$, —$OR_7$, —$COR_7$, —$COOR_3$, —$OCOOR_7$, —$OCON(R_7)_2$, —($C_1$-$C_8$)alkylene-$COOR_7$, —CN, —$NO_2$, —SH, —$SR_7$, —($C_1$-$C_8$)alkyl, —$N(R_7)_2$, —$CON(R_7)_2$, —$SO_2R_7$, $SO_2N(R_7)_2$, or —$S(=O)R_7$; or two $R_2$ groups and the carbon atom to which they are attached form a 5- or 6-membered carbocyclic or heterocyclic ring;

$R_3$ each independently is selected from ($C_1$-$C_8$)alkyl, ($C_2$-$C_8$)alkenyl, or ($C_2$-$C_8$)alkynyl;

$R_4$ is selected from H, —$COOR_3$, —($C_1$-$C_8$)alkylene-$COOR_7$, —CN, —($C_1$-$C_8$)alkyl, or —$CON(R_7)_2$;

$R_5$ is selected from H, —OH, —O—($C_1$-$C_8$)alkyl, —CO—($C_1$-$C_8$)alkyl, —COO—($C_1$-$C_8$)alkyl, —CN, or —$NH_2$;

$R_6$ each independently is selected from H, ($C_1$-$C_8$)alkyl, ($C_3$-$C_{10}$)cycloalkyl, 4-12-membered heterocyclyl, ($C_6$-$C_{14}$)aryl, or —($C_1$-$C_8$)alkylene-$NH_2$;

$R_7$ each independently is selected from H, ($C_1$-$C_8$)alkyl, —($C_1$-$C_8$)alkylene-$NH_2$, ($C_3$-$C_{10}$)cycloalkyl, 4-12-membered heterocyclyl, or ($C_6$-$C_{14}$)aryl, each of which other than H may optionally be substituted with —$OR_6$, —$COR_6$, —$COOR_6$, —$OCOOR_6$, —$OCON(R_6)_2$, —($C_1$-$C_8$)alkylene-$COOR_6$, —CN, —$NO_2$, —$SR_6$, —($C_1$-$C_8$)alkyl, —$N(R_6)_2$, —$CON(R_6)_2$, —$SO_2R_6$, or —$S(=O)R_6$; and n is an integer of 1 or 2.

In another aspect, the present invention relates to a pharmaceutical composition comprising a multifunctional nitroxide derivative of the general formula I as defined above, or an enantiomer, diastereomer, racemate, or a pharmaceutically acceptable salt, solvate or prodrug thereof, and a pharmaceutically acceptable carrier.

The multifunctional nitroxide derivatives and pharmaceutical compositions of the invention are useful for treatment, prevention and/or managing of diseases, disorders and conditions associated with high levels of reactive oxygen species (ROS) and oxidative stress. Thus, in a further aspect, the present invention provides a multifunctional nitroxide derivative of the general formula I as defined above, or an enantiomer, diastereomer, racemate, or a pharmaceutically acceptable salt, solvate or prodrug thereof, for use in treatment of a disease, disorder or condition associated with high levels of ROS, and oxidative stress.

In still another aspect, the present invention provides a method for treatment of a disease, disorder or condition associated with high levels of ROS, and oxidative stress, said method comprising administering to an individual in need a therapeutically effective amount of a multifunctional nitroxide derivative of the general formula I as defined above, or an enantiomer, diastereomer, racemate, or a pharmaceutically acceptable salt, solvate or prodrug thereof.

DETAILED DESCRIPTION OF THE PREFERRED EMBODIMENT

Figure 1:
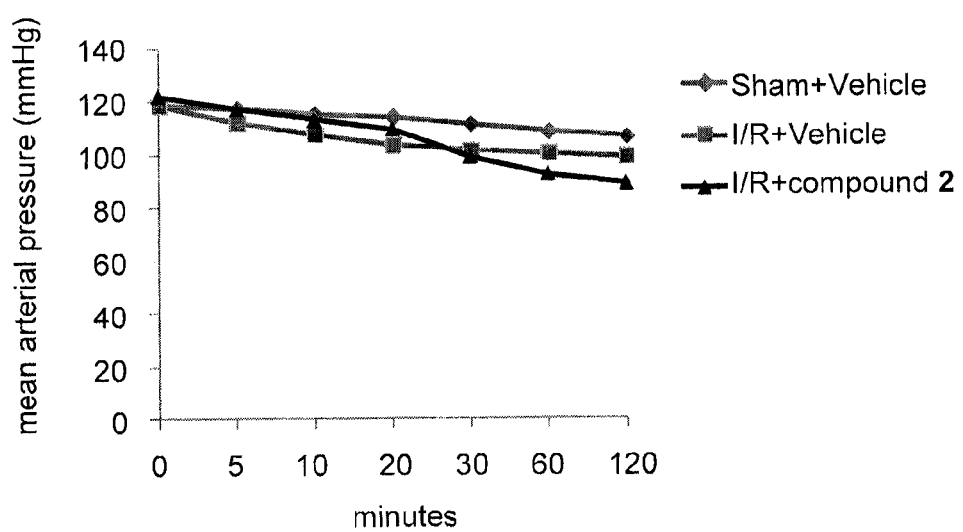
FIG. 1 shows the mean arterial pressure (mmHg) measured in rats subjected to a model of myocardial ischemia-reperfusion (PR) injury (MIRI) as described in Example 11, indicating that compound 2, when administered prior to reperfusion at 1 mg/kg IV bolus followed by a continuous IV infusion of 2 mg/kg/h, did not produce systemic hypotension.

The present invention provides chemical compounds of the general formula I as defined above, herein also termed "multifunctional nitroxide derivatives", comprising a potassium channel opener as well as a reactive oxygen species (ROS) degradation catalyst that can act as an anti-oxidant. The term "reactive oxygen species (ROS) degradation catalyst", as used herein, refers to a group capable of acting as a scavenger of, or catalytically detoxifying, superoxide or other ROS including superoxide, hydroxyl radicals, peroxynitrite, peroxycarbonate, hypochlorous acid, and hydrogen peroxide. An anti-oxidant that preferentially scavenges, or catalytically detoxifies, superoxide is termed a "superoxide dismutase mimic" ("SOD-mimic") or "superoxide dismutase mimetic" ("SOD-mimetic"). The ROS superoxide, hydroxyl radicals, peroxynitrite, peroxycarbonate, hypochlorous acid and hydrogen peroxide are considered biologically undesirable. This ROS degradation catalyst is a nitroxide free radical ($NO^-$) group.

The multifunctional nitroxide derivatives of the present invention are useful for the prevention and treatment of inflammatory and reperfusion diseases, disorders or conditions. By virtue of the potassium channel opener and ROS degrading activities being covalently linked, the compounds of the invention ensure that adding potassium channel opener is accompanied contemporaneously and spatially by reduced levels of ROS, including peroxynitrite, peroxycarbonate, hydrogen peroxide, hydroxyl radicals, and other oxidant metabolites thereof.

The term "halogen" as used herein includes fluoro, chloro, bromo, and iodo, and is preferably fluoro, chloro or bromo.

The term "alkyl" as used herein typically means a straight or branched saturated hydrocarbon radical having 1-8 carbon atoms and includes, e.g., methyl, ethyl, n-propyl, isopropyl, n-butyl, sec-butyl, isobutyl, tert-butyl, n-pentyl, 2,2-dimethylpropyl, n-hexyl, n-heptyl, n-octyl and the like. Preferred are ($C_1$-$C_6$)alkyl groups, more preferably ($C_1$-$C_4$) alkyl groups, most preferably methyl and ethyl. The terms "alkenyl" and "alkynyl" typically mean straight and branched hydrocarbon radicals having 2-8 carbon atoms and 1 double or triple bond, respectively, and include ethenyl, propenyl, 3-buten-1-yl, 2-ethenylbutyl, 3-octen-1-yl, and the like, and propynyl, 2-butyn-1-yl, 3-pentyn-1-yl, and the like. $C_2$-$C_6$ alkenyl and alkynyl radicals are preferred, more preferably $C_2$-$C_4$ alkenyl and alkynyl.

The term "alkylene" typically means a divalent straight or branched hydrocarbon radical having 1-8 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene and the like. Preferred are ($C_1$-$C_6$) alkylene, more preferably ($C_1$-$C_4$)alkylene, most preferably ($C_1$-$C_2$)alkylene.

The term "cycloalkyl" as used herein means a mono- or bicyclic saturated hydrocarbyl group having 3-10 carbon atoms such as cyclopropyl, cyclobutyl, cyclopentyl, cyclohexyl, cycloheptyl, cyclooctyl, adamantyl, bicyclo[3.2.1]octyl, bicyclo[2.2.1]heptyl, and the like, that may be substituted, for example, by one or more alkyl groups.

The term "carbocyclic ring" as used herein refers to a saturated or unsaturated, i.e., containing at least one unsaturated bond, ring consisting of 3-10 carbon atoms. Preferred are 5- or 6-membered carbocyclic rings such as cyclopentane, cyclopentene, cyclohexane, cyclohexene and the like.

The term "heterocyclic ring" denotes a mono- or polycyclic non-aromatic ring of 4-12 atoms containing at least one carbon atom and one to three, preferably 1-2 heteroatoms selected from sulfur, oxygen or nitrogen, which may be saturated or unsaturated, i.e., containing at least one unsaturated bond. Preferred are 5- or 6-membered heterocyclic rings. The term "heterocyclyl" as used herein refers to any univalent radical derived from a heterocyclic ring as defined herein by removal of hydrogen from any ring atom. Examples of such radicals include, without limitation, piperidino, 4-morpholinyl, or pyrrolidinyl.

The term "aryl" denotes an aromatic carbocyclic group having 6-14 carbon atoms consisting of a single ring or multiple rings either condensed or linked by a covalent bond such as, but not limited to, phenyl, naphthyl, phenanthryl, and biphenyl. The aryl radical may optionally be substituted by one or more groups each independently selected from halogen, e.g., F, Cl or Br, ($C_1$-$C_8$)alkyl, —O—($C_1$-$C_8$)alkyl, —COO($C_1$-$C_8$)alkyl, —CN, or $NO_2$.

The term "heteroaryl" refers to a radical derived from a mono- or poly-cyclic heteroaromatic ring containing one to three, preferably 1-2, heteroatoms selected from the group consisting of N, O and S. When the heteroaryl is a monocyclic ring, it is preferably a radical of a 5-6-membered ring such as, but not limited to, pyrrolyl, furyl, thienyl, thiazinyl, pyrazolyl, pyrazinyl, imidazolyl, oxazolyl, isoxazolyl, thiazolyl, isothiazolyl, pyridyl, pyrimidinyl, 1,2,3-triazinyl, 1,3,4-triazinyl, and 1,3,5-triazinyl. Polycyclic heteroaryl radicals are preferably composed of two rings such as, but not limited to, benzofuryl, isobenzofuryl, benzothienyl, indolyl, quinolinyl, isoquinolinyl, imidazo[1,2-c]pyridyl, benzimidazolyl, benzthiazolyl, benzoxazolyl, pyrido[1,2-a]pyrimidinyl and 1,3-benzodioxinyl. The heteroaryl may be substituted. It is to be understood that when a polycyclic heteroaryl is substituted, the substitution may be in any of the carbocyclic and/or heterocyclic rings.

In certain embodiments, the multifunctional nitroxide derivative of the present invention is a compound of the general formula I wherein Y is N, i.e., a compound in which group A is linked to position 2, 3, 4, 5 or 6 of a pyridine ring. Particular such compounds shown in Table 1 are those wherein A is linked to position 2, 3 or 4 of the pyridine ring, and (i) X is absent, i.e., the oxy radical of a 1-(1-hydroxypyrrolidin-3-yl)-3-(pyridin-2-yl)guanidine derivative, 1-(1-hydroxy pyrrolidin-3-yl)-3-(pyridin-3-yl)guanidine derivative, or 1-(1-hydroxypyrrolidin-3-yl)-3-(pyridin-4-yl) guanidine derivative (formula Ia-2, Ia-2 or Ia-3, respectively); (ii) X is —$(CR_2R_2)_n$— wherein n is 1, i.e., the oxy radical of a 1-(1-hydroxypiperidin-4-yl)-3-(pyridin-2-yl)guanidine derivative, 1-(1-hydroxypiperidin-4-yl)-3-(pyridin-3-yl)guanidine derivative, or 1-(1-hydroxy piperidin-4-yl)-3-(pyridin-4-yl)guanidine derivative (formula Ia-4, Ia-5 or Ia-6, respectively); or (iii) X is —$(CR_2R_2)_n$— wherein n is 2, i.e., the oxy radical of a 1-(1-hydroxyazepan-4-yl)-3-(pyridin-2-yl)guanidine derivative, 1-(1-hydroxyazepan-4-yl)-3-(pyridin-3-yl)guanidine derivative, or 1-(1-hydroxyazepan-4-yl)-3-(pyridin-4-yl)guanidine derivative (formula Ia-7, Ia-8, or Ia-9, respectively). More particular such compounds are those wherein A is linked to position 3 or 4 of the pyridine ring.

TABLE 1

Multifunctional nitroxide derivatives of the formulas Ia-1 to Ia-9

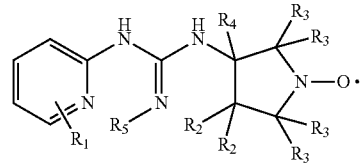

Ia-1

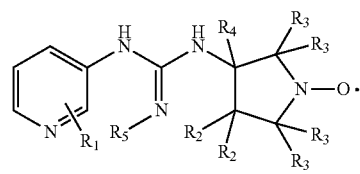

Ia-2

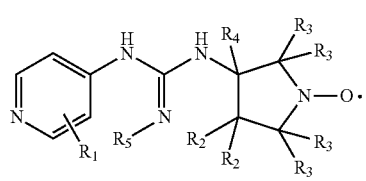

Ia-3

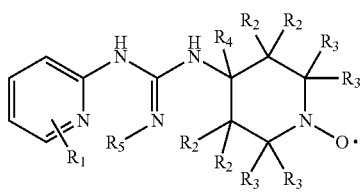

Ia-4

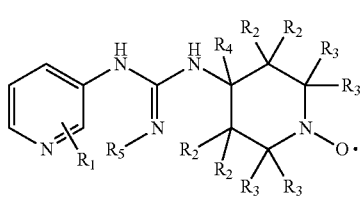

Ia-5

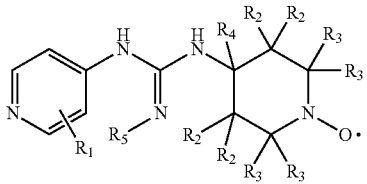

Ia-6

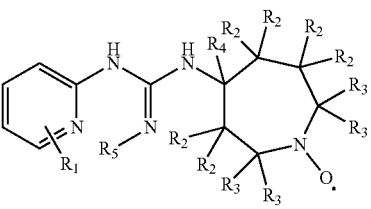

Ia-7

TABLE 1-continued

Multifunctional nitroxide derivatives of the formulas Ia-1 to Ia-9

Ia-8

Ia-9

In other embodiments, the multifunctional nitroxide derivative of the present invention is a compound of the general formula I wherein Y is CH, i.e., a compound in which group A is linked to any position of a phenyl ring. Particular such compounds shown in Table 2 are those wherein (i) X is absent, i.e., the oxy radical of a 1-(1-hydroxypyrrolidin-3-yl)-3-phenylguanidine derivative (formula Ib-1); (ii) X is —(CR$_2$R$_2$)$_n$— wherein n is 1, i.e., the oxy radical of a 1-(1-hydroxypiperidine-4-yl)-3-phenylguanidine derivative (formula Ib-2); or (iii) X is —(CR$_2$R$_2$)$_n$— wherein n is 2, i.e., the oxy radical of a 1-(1-hydroxyazepan-4-yl)-3-phenylguanidine derivative (formula Ib-3).

TABLE 2

Multifunctional nitroxide derivatives of the formulas Ib-1 to Ib-3

Ib-1

Ib-2

Ib-3

In further embodiments, the multifunctional nitroxide derivative of the present invention is a compound of the general formula I wherein Y is N(>O), i.e., a compound in which group A is linked to position 2, 3, 4, 5 or 6 of a pyridine oxide ring. Particular such compounds shown in Table 3 are those wherein A is linked to position 2, 3 or 4 of the pyridine oxide ring, and (i) X is absent, i.e., the oxy radical of a 1-(1-hydroxypyrrolidin-3-yl)-3-(1-oxypyridin-2-yl)guanidine derivative, 1-(1-hydroxypyrrolidin-3-yl)-3-(1-oxypyridin-3-yl)guanidine derivative, or 1-(1-hydroxypyrrolidin-3-yl)-3-(1-oxypyridin-4-yl)guanidine derivative (formula Ic-1, Ic-2 or Ic-3, respectively); (ii) X is —(CR$_2$R$_2$)$_n$— wherein n is 1, i.e., the oxy radical of a 1-(1-hydroxypiperidin-4-yl)-3-(1-oxypyridin-2-yl)guanidine derivative, 1-(1-hydroxypiperidin-4-yl)-3-(1-oxypyridin-3-yl)guanidine derivative, or 1-(1-hydroxy piperidin-4-yl)-3-(1-oxypyridin-4-yl)guanidine derivative (formula Ic-4, Ic-5 or Ic-6, respectively); or (iii) X is —(CR$_2$R$_2$)$_n$— wherein n is 2, i.e., the oxy radical of a 1-(1-hydroxyazepan-4-yl)-3-(1-oxypyridin-2-yl)guanidine derivative, 1-(1-hydroxyazepan-4-yl)-3-(1-oxypyridin-3-yl)guanidine derivative, or 1-(1-hydroxy azepan-4-yl)-3-(1-oxypyridin-4-yl)guanidine derivative (formula Ic-7, Ic-8 or Ic-9, respectively). More particular such compounds are those wherein A is linked to position 3 or 4 of the pyridine ring.

TABLE 3

Multifunctional nitroxide derivatives of the formulas Ic-1 to Ic-9

Ic-1

Ic-2

Ic-3

Ic-4

Ic-5

TABLE 3-continued

Multifunctional nitroxide derivatives of the formulas Ic-1 to Ic-9

Ic-6

Ic-7

Ic-8

Ic-9

According to the present invention, $R_1$ is absent or represents 1 to 5 substituents as defined above. Nevertheless, it should be understood that in cases wherein Y is N or N(→O), the maximal number of $R_1$ groups is limited to 4 only.

In certain embodiments, the multifunctional nitroxide derivative of the present invention is a compound of the general formulas Ia-1 to Ia-9, a compound of the general formula Ib-1 to Ib-3, or a compound of the general formula Ic-1 to Ic-9, wherein $R_1$ is absent.

In other embodiments, the multifunctional nitroxide derivative of the present invention is a compound of the general formulas Ia-1 to Ia-9, a compound of the general formula Ib-1 to Ib-3, or a compound of the general formula to Ic-9, wherein $R_1$ is 1, 2, 3, 4 or 5, preferably 1 or 2, more preferably 1, substituents each independently selected from halogen, —OH, —CN, —NO$_2$, —N(R$_6$)$_2$, —OR$_6$, —OCF$_3$, —CF$_3$, —COR$_6$, —COOR$_6$, —CON(R$_6$)$_2$, —OCOOR$_6$, —OCON(R$_6$)$_2$, —(C$_1$-C$_8$)alkylene-COOR$_6$, —SO$_2$R$_6$, —SO$_2$N(R$_6$)$_2$, or —S(=O)R$_6$, wherein $R_6$ each independently is H, (C$_1$-C$_8$)alkyl, or —(C$_1$-C$_8$)alkylene-NH$_2$, preferably H.

In further embodiments, the multifunctional nitroxide derivative of the present invention is a compound of the general formula Ia-1 to Ia-9, a compound of the general formula Ib-1 to Ib-3, or a compound of the general formula Ic-1 to Ic-9, wherein two adjacent $R_1$ groups and the carbon atoms of the pyridine ring to which they are attached form a 5- or 6-membered carbocyclic or heterocyclic ring, (C$_6$-C$_{10}$)aryl, or 6- to 10-membered heteroaryl. In such embodiments, group A in the general formula I is linked, in fact, to a pyridine-, phenyl-, or pyridine oxide-moiety condensed to a monocyclic or bicyclic group selected from a 5- or 6-membered carbocyclic or heterocyclic ring, (C$_6$-C$_{10}$)aryl, or 6- to 10-membered heteroaryl. Non-limiting examples of such multifunctional nitroxide derivatives include (i) compounds of the general formula I wherein Y is N, in which group A is linked to a moiety of 6,7,dihydro-5H-cyclopenta[b]pyridine, 6,7,dihydro-5H-cyclopenta[c]pyridine, 5,6,7,8-tetrahydro quinoline, 5,6,7,8-tetrahydroisoquinoline, 2,3-dihydrofuro[3,2-b]pyridine, 3,4-dihydro-2H-pyrano[3,2-b]pyridine, quinoline, isoquinoline, benzo[g]quinoline, benzo[g]isoquinoline, 1,5-naphthyridine, 1,8-naphtyridine, pyrido[2,3-b]pyrazine, or pyrido[3,2-g]quinolone; (ii) compounds of the general formula I wherein Y is CH, in which group A is linked to a moiety of 2,3-dihydro-1H-indene, 1,2,3,4-tetrahydronaphthalene, 2,3-dihydrobenzofuran, chroman, naphthalene, anthracene, quinoline, quinoxaline, or benzo[g]quinoline; and (iii) compounds of the general formula I wherein Y is N(→O), in which group A is linked to a moiety of 1-oxy-6,7,dihydro-5H-cyclopenta[b]pyridine, 2-oxy-6,7,dihydro-5H-cyclopenta[c]pyridine, 1-oxy-5,6,7,8-tetrahydro quinoline, 2-oxy-5,6,7,8-tetrahydroisoquinoline, 4-oxy-2,3-dihydrofuro[3,2-b]pyridine, 5-oxy-3,4-dihydro-2H-pyrano[3,2-b]pyridine, 1-oxyquinoline, 2-oxyisoquinoline, 1-oxybenzo[g]quinoline, 2-oxybenzo[g]isoquinoline, 1-oxy-1,5-naphthyridine, 1-oxy-1,8-naphthyridine, 5-oxypyrido[2,3-b]pyrazine, or 1-oxypyrido[3,2-g]quinoline.

In certain embodiments, the multifunctional nitroxide derivative of the present invention is a compound of the general formulas Ia-1 to Ia-9, a compound of the general formula Ib-1 to Ib-3, or a compound of the general formula Ic-1 to Ic-9, wherein $R_2$ each is H.

In certain embodiments, the multifunctional nitroxide derivative of the present invention is a compound of the general formulas Ia-1 to Ia-9, a compound of the general formula Ib-1 to Ib-3, or a compound of the general formula Ic-4 to Ic-9, wherein $R_3$ each independently is (C$_1$-C$_4$)alkyl, preferably (C$_1$-C$_2$)alkyl, more preferably methyl. In particular such embodiments, the multifunctional nitroxide derivative of the invention is such a compound, wherein $R_3$ are identical.

In certain embodiments, the multifunctional nitroxide derivative of the present invention is a compound of the general formulas Ia-1 to Ia-9, a compound of the general formula Ib-1 to Ib-3, or a compound of the general formula Ic-1 to Ic-9, wherein $R_4$ is H.

In certain embodiments, the multifunctional nitroxide derivative of the present invention is a compound of the general formulas Ia-1 to Ia-9, a compound of the general formula Ib-1 to Ib-3, or a compound of the general formula Ic-1 to Ic-9, wherein $R_5$ is —CN.

In certain particular embodiments, the multifunctional nitroxide derivative of the present invention is a compound of the general formula I, wherein Y is N; A is linked to position 2, 3, 4, 5 or 6 of the pyridine ring; $R_1$ is absent or 1 to 4 substituents each independently is halogen; X is absent or —(CR$_2$R$_2$)$_n$— wherein n is 1 or 2; $R_2$ each is H; $R_3$ each independently is (C$_1$-C$_4$)alkyl, preferably (C$_1$-C$_2$) alkyl, more preferably methyl; $R_4$ is H; and $R_5$ is —CN. In certain more particular embodiments, $R_1$ is a sole substituent linked to any of the available carbon atoms of the pyridine ring, i.e., a halogen linked to the pyridine ring at position ortho, meta or para with respect to group A. In other more particular embodiments, $R_1$ represents 2 substituents each independently linked to any of the available carbon atoms of the pyridine ring, i.e., two halogens linked to the pyridine ring at position ortho, meta or para with respect to each other. Specific such compounds described in the specification are herein identified by the Arabic numbers 1-21 in bold (each one of the compounds 4-7, 11-14 and 18-21 has three configurations identified a-c), wherein their full chemical structures are depicted in Table 4 hereinafter.

In certain specific embodiments, the multifunctional nitroxide derivative of the invention is a compound of the general formula I, wherein Y is N; X is absent; $R_1$ is absent; $R_2$ is H; $R_3$ is methyl; and A is linked to position 2, 3 or 4 of the pyridine ring, i.e., the oxy radical of 2-cyano-1-(1-hydroxy-2,2,5,5-tetramethyl pyrrolidin-3-yl)-3-(pyridin-2-yl)guanidine (compound 1); 2-cyano-1-(1-hydroxy-2,2,5,5-tetramethylpyrrolidin-3-yl)-3-(pyridin-3-yl)guanidine (compound 2); or 2-cyano-1-(1-hydroxy-2,2,5,5-tetramethylpyrrolidin-3-yl)-3-(pyridin-4-yl)guanidine (compound 3).

In other specific embodiments, the multifunctional nitroxide derivative of the invention is a compound of the general formula I, wherein Y is N; X is absent; $R_1$ is F, Cl or Br, linked to position 6 of the pyridine ring; $R_2$ is H; $R_3$ is methyl; and A is linked to position 2, 3, 4 or 5 of the pyridine ring, i.e., the oxy radical of 2-cyano-1-(6-fluoropyridin-2-yl)-3-(1-hydroxy-2,2,5,5-tetramethylpyrrolidin-3-yl)guanidine, 2-cyano-1-(6-chloropyridin-2-yl)-3-(1-hydroxy-2,2,5,5-tetramethyl pyrrolidin-3-yl)guanidine, or 2-cyano-1-(6-bromopyridin-2-yl)-3-(1-hydroxy-2,2,5,5-tetramethylpyrrolidin-3-yl)guanidine (compounds $4_a$-$4_c$, respectively); 2-cyano-1-(6-fluoropyridin-3-yl)-3-(1-hydroxy-2,2,5,5-tetramethylpyrrolidin-3-yl)guanidine, 2-cyano-1-(6-chloropyridin-3-yl)-3-(1-hydroxy-2,2,5,5-tetramethyl pyrrolidin-3-yl)guanidine, or 2-cyano-1-(6-bromopyridin-3-yl)-3-(1-hydroxy-2,2,5,5-tetramethylpyrrolidin-3-yl)guanidine (compounds $5_a$-$5_c$, respectively); 2-cyano-1-(6-fluoropyridin-4-yl)-3-(1-hydroxy-2,2,5,5-tetramethylpyrrolidin-3-yl)guanidine, 2-cyano-1-(6-chloropyridin-4-yl)-3-(1-hydroxy-2,2,5,5-tetramethyl pyrrolidin-3-yl)guanidine, or 2-cyano-1-(6-bromopyridin-4-yl)-3-(1-hydroxy-2,2,5,5-tetramethylpyrrolidin-3-yl)guanidine (compounds $6_a$-$6_c$, respectively); or 2-cyano-1-(6-fluoropyridin-5-yl)-3-(1-hydroxy-2,2,5,5-tetramethylpyrrolidin-3-yl)guanidine, 2-cyano-1-(6-chloropyridin-5-yl)-3-(1-hydroxy-2,2,5,5-tetramethyl pyrrolidin-3-yl)guanidine, or 2-cyano-1-(6-bromopyridin-5-yl)-3-(1-hydroxy-2,2,5,5-tetramethylpyrrolidin-3-yl)guanidine (compounds $7_a$-$7_c$, respectively).

In further specific embodiments, the multifunctional nitroxide derivative of the invention is a compound of the general formula I, wherein Y is N; X is —$(CR_2R_2)_n$— wherein n is 1; $R_1$ is absent; $R_2$ is H; $R_3$ is methyl; and A is linked to position 2, 3 or 4 of the pyridine ring, i.e., the oxy radical of 2-cyano-1-(1-hydroxy-2,2,6,6-tetramethylpiperidin-4-yl)-3-(pyridin-2-yl)guanidine (compound 8); 2-cyano-1-(1-hydroxy-2,2,6,6-tetramethylpiperidin-4-yl)-3-(pyridin-3-yl)guanidine (compound 9); or 2-cyano-1-(1-hydroxy-2,2,6,6-tetramethylpiperidin-4-yl)-3-(pyridin-4-yl)guanidine (compound 10).

In still other specific embodiments, the multifunctional nitroxide derivative of the invention is a compound of the general formula I, wherein Y is N; X is —$(CR_2R_2)$— wherein n is 1; $R_1$ is F, Cl or Br, linked to position 6 of the pyridine ring; $R_2$ is H; $R_3$ is methyl; and A is linked to position 2, 3, 4 or 5 of the pyridine ring, i.e., the oxy radical of 2-cyano-1-(6-fluoropyridin-2-yl)-3-(1-hydroxy-2,2,6,6-tetramethylpiperidin-4-yl)guanidine, 2-cyano-1-(6-chloropyridin-2-yl)-3-(1-hydroxy-2,2,6,6-tetramethylpiperidin-4-yl)guanidine, or 2-cyano-1-(6-bromo pyridin-2-yl)-3-(1-hydroxy-2,2,6,6-tetramethylpiperidin-4-yl)guanidine (compounds $11_a$-$11_c$, respectively); 2-cyano-1-(6-fluoropyridin-3-yl)-3-(1-hydroxy-2,2,6,6-tetramethylpiperidin-4-yl)guanidine, 2-cyano-1-(6-chloropyridin-3-yl)-3-(1-hydroxy-2,2,6,6-tetramethylpiperidin-4-yl)guanidine, or 2-cyano-1-(6-bromo pyridin-3-yl)-3-(1-hydroxy-2,2,6,6-tetramethylpiperidin-4-yl)guanidine (compounds $12_a$-$12_c$, respectively); 2-cyano-1-(6-fluoropyridin-4-yl)-3-(1-hydroxy-2,2,6,6-tetramethylpiperidin-4-yl)guanidine, 2-cyano-1-(6-chloropyridin-4-yl)-3-(1-hydroxy-2,2,6,6-tetramethylpiperidin-4-yl)guanidine, or 2-cyano-1-(6-bromo pyridin-4-yl)-3-(1-hydroxy-2,2,6,6-tetramethylpiperidin-4-yl)guanidine (compounds $13_a$-$13_c$, respectively); or 2-cyano-1-(6-fluoropyridin-5-yl)-3-(1-hydroxy-2,2,6,6-tetramethylpiperidin-4-yl)guanidine, 2-cyano-1-(6-chloropyridin-5-yl)-3-(1-hydroxy-2,2,6,6-tetramethylpiperidin-4-yl)guanidine, or 2-cyano-1-(6-bromopyridin-5-yl)-3-(1-hydroxy-2,2,6,6-tetramethylpiperidin-4-yl)guanidine (compounds $14_a$-$14_c$, respectively).

In yet other specific embodiments, the multifunctional nitroxide derivative of the invention is a compound of the general formula I, wherein Y is N; X is —$(CR_2R_2)_n$— wherein n is 2; $R_1$ is absent; $R_2$ is H; $R_3$ is methyl; and A is linked to position 2, 3 or 4 of the pyridine ring, i.e., the oxy radical of 2-cyano-1-(1-hydroxy-2,2,7,7-tetramethylazepan-4-yl)-3-(pyridin-2-yl)guanidine (compound 15); 2-cyano-1-(1-hydroxy-2,2,7,7-tetramethylazepan-4-yl)-3-(pyridin-3-yl)guanidine (compound 16); or 2-cyano-1-(1-hydroxy-2,2,7,7-tetramethylazepan-4-yl)-3-(pyridin-4-yl)guanidine (compound 17).

TABLE 4

Multifunctional nitroxide derivatives herein identified compounds 1-21

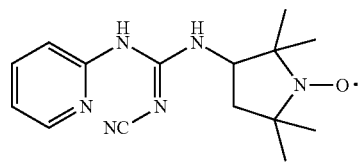

1

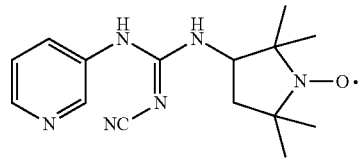

2

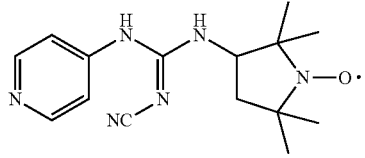

3

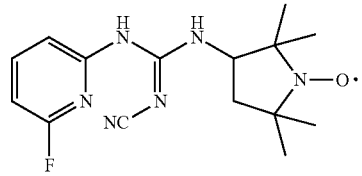

$4_a$*

TABLE 4-continued

Multifunctional nitroxide derivatives herein identified compounds 1-21

| Compound | | Compound | |
|---|---|---|---|
| 5$_a$* | | 14$_a$* | |
| 6$_a$* | | 15 | |
| 7$_a$* | | 16 | |
| 8 | | 17 | |
| 9 | | 18$_a$* | |
| 10 | | 19$_a$* | |
| 11$_a$* | | 20$_a$* | |
| 12$_a$* | | 21$_a$* | |
| 13$_a$* | | | |

*The compound in which the F atom is replaced by Cl or Br has the same identification number with configuration "b" or "c", respectively In yet further specific embodiments, the multifunctional nitroxide derivative of the invention is a compound of the general formula I, wherein Y is N; X is —(CR$_2$R$_2$)$_n$— wherein n is 2; R$_1$ is F, Cl or Br, linked to position 6 of the pyridine ring; R$_2$ is H; R$_3$ is methyl; and A is linked to position 2, 3, 4 or 5 of the pyridine ring, i.e., the oxy radical of 2-cyano-1-(6-fluoropyridin-2-yl)-3-(1-hydroxy-2,2,7,7-tetramethylazepan-4-yl)guanidine, 2-cyano-1-(6-chloropyridin-2-yl)-3-(1-hydroxy-2,2,7,7-tetramethylazepan-4-yl) guanidine, or 2-cyano-1-(6-bromopyridin-2-yl)-3-(1-hydroxy-2,2,7,7-tetramethylazepan-4-yl)guanidine (compounds 18$_a$-18$_c$, respectively); 2-cyano-1-(6-fluoropyridin-3-yl)-3-(1-hydroxy-2,2,7,7-tetramethylazepan-4-yl) guanidine, 2-cyano-1-(6-chloropyridin-3-yl)-3-(1-hydroxy-2,2,7,7-tetra methyl azepan-4-yl)guanidine, or 2-cyano-1-(6-bromopyridin-3-yl)-3-(1-hydroxy-2,2,7,7-tetramethylazepan-4-yl)guanidine (compounds 19$_a$-19$_c$, respectively); 2-cyano-1-(6-fluoropyridin-4-yl)-3-(1-hydroxy-2,2,7,7-tetramethylazepan-4-yl)guanidine, 2-cyano-1-(6-chloropyridin-4-yl)-3-(1-hydroxy-2,2,7,7-tetramethylazepan-4-yl)guanidine, or 2-cyano-1-(6-bromopyridin-4-yl)-3-(1-hydroxy-2,2,7,7-tetramethylazepan-4-yl)guanidine (compounds 20$_a$-20$_c$, respectively); or 2-cyano-1-(6-fluoropyridin-5-yl)-3-(1-hydroxy-2,2,7,7-tetramethylazepan-4-yl) guanidine, 2-cyano-1-(6-chloropyridin-5-yl)-3-(1-hydroxy-2,2,7,7-tetramethylazepan-4-yl)guanidine, or 2-cyano-1-(6-bromopyridin-5-yl)-3-(1-hydroxy-2,2,7,7-tetramethylazepan-4-yl)guanidine (compounds 21$_a$-21$_c$, respectively).

In certain particular embodiments, the multifunctional nitroxide derivative of the present invention is a compound of the general formula I, wherein Y is CH; A is linked to any position of the phenyl ring; R$_1$ is absent or 1 to 5 substituents each independently is halogen; X is absent or —(CR$_2$R$_2$)$_n$— wherein n is 1 or 2; R$_2$ each is H; R$_3$ each independently is (C$_1$-C$_4$)alkyl, preferably (C$_1$-C$_2$)alkyl, more preferably methyl; R$_4$ is H; and R$_5$ is —CN. In certain more particular embodiments, R$_1$ is a sole substituent linked to any of the available carbon atoms of the phenyl ring, i.e., a halogen linked to the phenyl ring at position ortho, meta or para with respect to group A. In other more particular embodiments, R$_1$ represents 2 substituents each independently linked to any of the available carbon atoms of the phenyl ring, i.e., two halogens linked to the phenyl ring at position ortho, meta or para with respect to each other. Specific such compounds described in the specification are herein identified by the Arabic numbers 22-39 in bold (each one of the compounds 23-25, 33-35 and 37-39 has three configurations identified a-c), wherein their full chemical structures are depicted in Table 5 hereinafter.

In a specific embodiment, the multifunctional nitroxide derivative of the invention is a compound of the general formula I, wherein Y is CH; X is absent; R$_1$ is absent; R$_2$ is H; and R$_3$ is methyl, i.e., the oxy radical of 2-cyano-1-(1-hydroxy-2,2,5,5-tetramethylpyrrolidin-3-yl)-3-phenyl guanidine (compound 22).

In other specific embodiments, the multifunctional nitroxide derivative of the invention is a compound of the general formula I, wherein Y is CH; X is absent; R$_2$ is H; R$_3$ is methyl; and R$_1$ is F, Cl or Br, linked to the phenyl ring at position ortho, meta or para with respect to A, i.e., the oxy radical of 2-cyano-1-(2-fluoro phenyl)-3-(1-hydroxy-2,2,5,5-tetramethylpyrrolidin-3-yl)guanidine, 2-cyano-1-(2-chlorophenyl)-3-(1-hydroxy-2,2,5,5-tetramethylpyrrolidin-3-yl)guanidine, or 2-cyano-1-(2-bromophenyl)-3-(1-hydroxy-2,2,5,5-tetramethylpyrrolidin-3-yl)guanidine (compounds 23$_a$-23$_c$, respectively); 2-cyano-1-(3-fluorophenyl)-3-(1-hydroxy-2,2,5,5-tetramethylpyrrolidin-3-yl)guanidine, 2-cyano-1-(3-chlorophenyl)-3-(1-hydroxy-2,2,5,5-tetramethylpyrrolidin-3-yl)guanidine, or 2-cyano-1-(3-bromo phenyl)-3-(1-hydroxy-2,2,5,5-tetramethylpyrrolidin-3-yl) guanidine (compounds 24$_a$-24$_c$, respectively); or 2-cyano-1-(4-fluorophenyl)-3-(1-hydroxy-2,2,5,5-tetramethylpyrrolidin-3-yl)guanidine, 2-cyano-1-(4-chlorophenyl)-3-(1-hydroxy-2,2,5,5-tetramethylpyrrolidin-3-yl)guanidine, or 2-cyano-1-(4-bromophenyl)-3-(1-hydroxy-2,2,5,5-tetramethylpyrrolidin-3-yl)guanidine (compounds 25$_a$-25$_c$, respectively).

In further specific embodiments, the multifunctional nitroxide derivative of the invention is a compound of the general formula I, wherein Y is CH; X is absent; R$_2$ is H; R$_3$ is methyl; and R$_1$ represents 2 substituents each independently is F, Cl or Br, linked to the phenyl ring at position ortho, meta or para with respect to A. In particular such embodiments, the multifunctional nitroxide derivative of the invention is a compound of the general formula I, wherein R$_1$ represents 2 substituents each is Cl, linked to the phenyl ring at positions ortho and ortho, i.e., the oxy radical of 2-cyano-1-(2,6-dichlorophenyl)-3-(1-hydroxy-2,2,5,5-tetramethyl pyrrolidin-3-yl)guanidine (compound 26); ortho and meta, i.e., the oxy radical of 2-cyano-1-(2,5-dichlorophenyl)-3-(1-hydroxy-2,2,5,5-tetramethylpyrrolidin-3-yl) guanidine or 2-cyano-1-(2,3-dichlorophenyl)-3-(1-hydroxy-2,2,5,5-tetramethyl pyrrolidin-3-yl)guanidine (compounds 27 and 28, respectively); ortho and para, i.e., the oxy radical of 2-cyano-1-(2,4-dichlorophenyl)-3-(1-hydroxy-2,2,5,5-tetramethyl pyrrolidin-3-yl)guanidine (compound 29); meta and meta, i.e., the oxy radical of 2-cyano-1-(3,5-dichlorophenyl)-3-(1-hydroxy-2,2,5,5-tetramethylpyrrolidin-3-yl) guanidine (compound 30); or meta and para, i.e., the oxy radical of 2-cyano-1-(3,4-dichlorophenyl)-3-(1-hydroxy-2,2,5,5-tetramethylpyrrolidin-3-yl)guanidine (compound 31), with respect to A.

In another specific embodiment, the multifunctional nitroxide derivative of the invention is a compound of the general formula I, wherein Y is CH; X is —(CR$_2$R$_2$)$_n$— wherein n is 1; R$_1$ is absent; R$_2$ is H; and R$_3$ is methyl, i.e., the oxy radical of 2-cyano-1-(1-hydroxy-2,2,6,6-tetramethylpiperidin-4-yl)-3-phenyl guanidine (compound 32).

In still other specific embodiments, the multifunctional nitroxide derivative of the invention is a compound of the general formula I, wherein Y is CH; X is —(CR$_2$R$_2$)$_n$— wherein n is 1; R$_2$ is H; R$_3$ is methyl; and R$_1$ is F, Cl or Br, linked to the phenyl ring at position ortho, meta or para with respect to A, i.e., the oxy radical of 2-cyano-1-(2-fluorophenyl)-3-(1-hydroxy-2,2,6,6-tetramethylpiperidin-4-yl)guanidine, 2-cyano-1-(2-chlorophenyl)-3-(1-hydroxy-2,2,6,6-tetramethylpiperidin-4-yl)guanidine, or 2-cyano-1-(2-bromophenyl)-3-(1-hydroxy-2,2,6,6-tetramethyl piperidin-4-yl)guanidine (compounds 33$_{a-c}$, respectively); 2-cyano-1-(3-fluoro phenyl)-3-(1-hydroxy-2,2,6,6-tetramethylpiperidin-4-yl)guanidine, 2-cyano-1-(3-chlorophenyl)-3-(1-hydroxy-2,2,6,6-tetramethylpiperidin-4-yl)guanidine, or 2-cyano-1-(3-bromophenyl)-3-(1-hydroxy-2,2,6,6-tetramethylpiperidin-4-yl) guanidine (compounds 34$_{a-c}$, respectively); or 2-cyano-1-(4-fluorophenyl)-3-(1-hydroxy-2,2,6,6-tetramethylpiperidin-4-yl) guanidine, 2-cyano-1-(4-chlorophenyl)-3-(1-hydroxy-2,2,6,6-tetramethylpiperidin-4-yl)guanidine, or 2-cyano-1-(4-bromo phenyl)-3-(1-hydroxy-2,2,6,6-tetramethylpiperidin-4-yl)guanidine (compounds 35$_{a-c}$, respectively).

In yet other specific embodiments, the multifunctional nitroxide derivative of the invention is a compound of the general formula I, wherein Y is CH; X is —(CR$_2$R$_2$)$_n$— wherein n is 1; R$_2$ is H; R$_3$ is methyl; and R$_1$ represents 2 substituents each independently is F, Cl or Br, linked to the phenyl ring at position ortho, meta or para with respect to A.

In a further specific embodiment, the multifunctional nitroxide derivative of the invention is a compound of the general formula I, wherein Y is CH; X is —(CR$_2$R$_2$)$_n$— wherein n is 2; R$_1$ is absent; R$_2$ is H; and R$_3$ is methyl, i.e., the oxy radical of 2-cyano-1-(1-hydroxy-2,2,7,7-tetramethylazepan-4-yl)-3-phenylguanidine (compound 36).

In still further specific embodiments, the multifunctional nitroxide derivative of the invention is a compound of the general formula I, wherein Y is CH; X is —(CR$_2$R$_2$)$_n$— wherein n is 2; R$_2$ is H; R$_3$ is methyl; and R$_1$ is F, Cl or Br, linked to the phenyl ring at position ortho, meta or para with respect to A, i.e., the oxy radical of 2-cyano-1-(2-fluorophenyl)-3-(1-hydroxy-2,2,7,7-tetramethylazepan-4-yl)guanidine, 2-cyano-1-(2-chlorophenyl)-3-(1-hydroxy-2,2,7,7-tetramethylazepan-4-yl)guanidine, or 2-cyano-1-(2-bromophenyl)-3-(1-hydroxy-2,2,7,7-tetra methylazepan-4-yl)guanidine (compounds 37$_{a-c}$, respectively); 2-cyano-1-(3-fluoro phenyl)-3-(1-hydroxy-2,2,7,7-tetramethylazepan-4-yl)guanidine, 2-cyano-1-(3-chlorophenyl)-3-(1-hydroxy-2,2,7,7-tetramethylazepan-4-yl)guanidine, or 2-cyano-1-(3-bromophenyl)-3-(1-hydroxy-2,2,7,7-tetramethylazepan-4-yl)guanidine (compounds 38$_{a-c}$, respectively); or 2-cyano-1-(4-fluorophenyl)-3-(1-hydroxy-2,2,7,7-tetramethylazepan-4-yl)guanidine, 2-cyano-1-(4-chlorophenyl)-3-(1-hydroxy-2,2,7,7-tetramethylazepan-4-yl)guanidine, or 2-cyano-1-(4-bromophenyl)-3-(1-hydroxy-2,2,7,7-tetramethylazepan-4-yl)guanidine (compounds 39$_{a-c}$, respectively).

In yet further specific embodiments, the multifunctional nitroxide derivative of the invention is a compound of the general formula I, wherein Y is CH; X is —(CR$_2$R$_2$)$_n$— wherein n is 1; R$_2$ is H; R$_3$ is methyl; and R$_1$ represents 2 substituents each independently is F, Cl or Br, linked to the phenyl ring at position ortho, meta or para with respect to A.

TABLE 5

Multifunctional nitroxide derivatives herein identified compounds 22-39

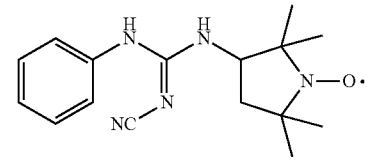

22

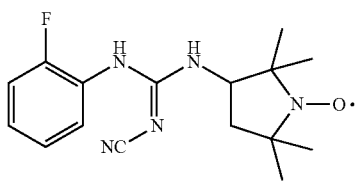

23$_a$*

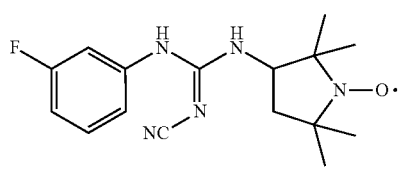

24$_a$*

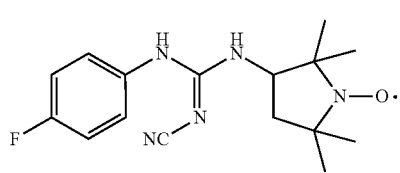

25$_a$*

TABLE 5-continued

Multifunctional nitroxide derivatives herein identified compounds 22-39

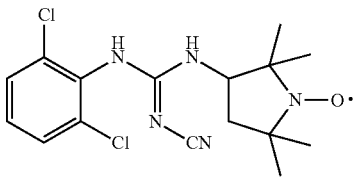

26

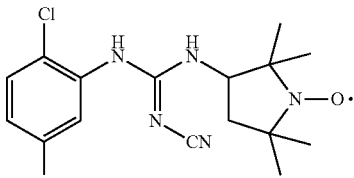

27

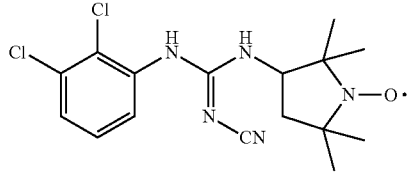

28

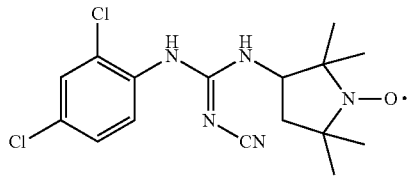

29

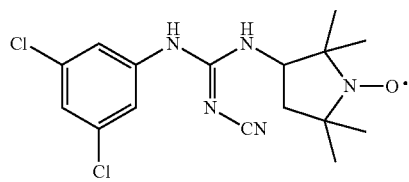

30

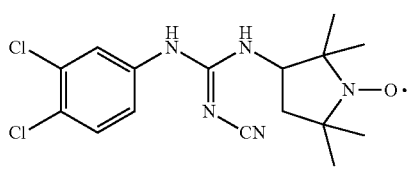

31

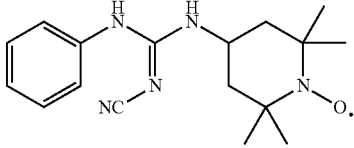

32

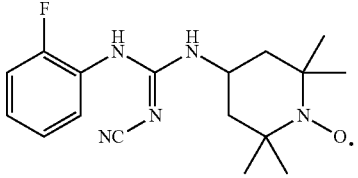

33$_a$*

TABLE 5-continued

Multifunctional nitroxide derivatives herein
identified compounds 22-39

| | |
|---|---|
| [structure] | $34_a$* |
| [structure] | $35_a$* |
| [structure] | 36 |
| [structure] | $37_a$* |
| [structure] | $38_a$* |
| [structure] | $39_a$* |

*The compound in which the F atom is replaced by Cl or Br has the same identification number with configuration "b" or "c", respectively In certain particular embodiments, the multifunctional nitroxide derivative of the present invention is a compound of the general formula I, wherein Y is N(→O); A is linked to position 2, 3, 4, 5 or 6 of the pyridine ring; $R_1$ is absent or 1 to 4 substituents each independently is halogen; X is absent or —$(CR_2R_2)_n$— wherein n is 1 or 2; $R_2$ each is H; $R_3$ each independently is $(C_1-C_4)$alkyl, preferably $(C_1-C_2)$ alkyl, more preferably methyl; $R_4$ is H; and $R_5$ is —CN. In certain more particular embodiments, $R_1$ is a sole substituent linked to any of the available carbon atoms of the pyridine oxide ring, i.e., a halogen linked to the pyridine oxide ring at position ortho, meta or para with respect to group A. In other more particular embodiments, $R_1$ represents 2 substituents each independently linked to any of the available carbon atoms of the pyridine oxide ring, i.e., two halogens linked to the pyridine oxide ring at position ortho, meta or para with respect to each other.

The various multifunctional nitroxide derivatives of the present invention may be synthesized according to any technology or procedure known in the art, e.g., as described in the Examples section hereinafter.

The multifunctional nitroxide derivatives of the present invention may have one or more asymmetric centers, and may accordingly exist both as enantiomers, i.e., optical isomers (R, S, or racemate, wherein a certain enantiomer may have an optical purity of 90%, 95%, 99% or more) and as diastereoisomers. Specifically, those chiral centers may be, e.g., in each one of the carbon atoms of the oxy radical of 1-hydroxypyrrolidin-3-yl, 1-hydroxypiperidin-4-yl, or 1-hydroxyazepan-4-yl moiety; as well as in either or both the —NH groups of the guanidino moiety. It should be understood that the present invention encompasses all such enantiomers, isomers and mixtures thereof, as well as pharmaceutically acceptable salts, solvates and prodrugs thereof.

Optically active forms of the multifunctional nitroxide derivatives of the invention may be prepared using any method known in the art, e.g., by resolution of the racemic form by recrystallization techniques; by chiral synthesis; by extraction with chiral solvents; or by chromatographic separation using a chiral stationary phase. A non-limiting example of a method for obtaining optically active materials is transport across chiral membranes, i.e., a technique whereby a racemate is placed in contact with a thin membrane barrier, the concentration or pressure differential causes preferential transport across the membrane barrier, and separation occurs as a result of the non-racemic chiral nature of the membrane that allows only one enantiomer of the racemate to pass through. Chiral chromatography, including simulated moving bed chromatography, can also be used. A wide variety of chiral stationary phases are commercially available.

As stated above, administration of compound 2 was found to be highly beneficial in treatment, prevention and/or managing of various diseases, disorders or conditions associated with oxidative stress or endothelial dysfunction.

As shown in Example 11, compound 2 significantly reduced both myocardial myeloperoxidase (MPO) and tissue infarction in a rat model of myocardial ischemia-reperfusion injury (MIRI). In particular, whereas MIRI induced severe myocyte necrosis, edema and neutrophil infiltration (center) compared to a sham control, administration of compound 2 prior to reperfusion profoundly attenuated virtually all histologic features of injury. Furthermore, in an ex vivo rat vascular ring system precontracted with norepinephrine, compound 2 was found to be a less potent ex vivo vasodilator compared to pinacidil, having $ED_{50}$ that is one log greater than that of pinacidil, indicative of a loss in sarcolemmal $K^+$-ATP channel activation.

Example 12 shows that compound 2 was further protective in a murine model of renal ischemia-reperfusion injury. More particularly, addition of compound 2 to CD mice underwent bilateral clamping of the renal pedicles, before reperfusion, profoundly attenuated elevations in plasma blood urea nitrogen and creatinine, as well as in renal meyloperoxidase, a marker of neutrophil' infiltration; and as revealed by histologic studies, provided near total protection against severe renal tubular necrosis.

In addition to its therapeutic properties in ischemia-reperfusion injury model, compound 2 has further been found to be effective as a rescue therapy in a murine model of acute chlorine inhalation injury as demonstrated in Example 13. As particularly shown, compound 2 administered to Balb/c mice 15 min after a continuous exposure to chlorine remarkably reduced both the elevation in polymorphonuclear leukocytes (PMN) infiltration as reflected in the level of myocardial myeloperoxidase (MPO) and histologic lung damage. As further shown, compound 2 attenuated lung injury in a dose-dependent manner, as exemplified by improved histology scores.

Example 14 shows that compound 2 did not exhibit any significant effect on blood glucose levels compared with saline vehicle group.

In another aspect, the present invention thus provides a pharmaceutical composition comprising a multifunctional nitroxide derivative of the general formula I as defined above, or an enantiomer, diastereomer, racemate, or a pharmaceutically acceptable salt, solvate or prodrug thereof, and a pharmaceutically acceptable carrier. In particular embodiments, the pharmaceutical composition of the invention comprises a multifunctional nitroxide derivative selected from compounds 1-39, or an enantiomer, diastereomer, racemate, or a pharmaceutically acceptable salt, solvate or prodrug thereof.

The multifunctional nitroxide derivatives and compositions of the present invention can be provided in a variety of formulations, e.g., in a pharmaceutically acceptable form and/or in a salt or solvate, e.g., hydrate, form, as well as in a variety of dosages. The multifunctional nitroxide derivatives of the invention can also be provided in the form of pharmaceutically acceptable prodrugs.

The term "prodrug" as used herein refers to a compound that can be metabolized or converted in vivo to provide a multifunctional nitroxide derivative of the general formula I as defined above, a process termed bioactivation. The rationale behind the use of prodrugs is generally for absorption, distribution, metabolism, and excretion optimization, wherein prodrugs are usually designed to improve oral bioavailability, with poor absorption from the gastrointestinal tract usually being the limiting factor, and/or to increase the selectivity of the drug for its intended target. Non-limiting examples of prodrugs according to the present invention include compounds that are prepared by adding ester, carbamate, carbonate, or benzyl group to the pyridine, phenyl oe pyridine oxide ring, or to the cyanoguanidine moiety in a multifunctional nitroxide derivative of the general formula I, via either an appropriate heteroatom or a linker, to provide a corresponding compound that can be metabolized or converted in vivo to provide said multifunctional nitroxide derivative. Examples for such modifications may be found, e.g., in Horino et al., Novel potassium channel opener prodrugs with a slow onset and prolonged duration of action, *Chem. Pharm. Bull.* (*Tokyo*), 2000, 48 (4), 490-495; and Uematsu et al., Pharmacokinetics and safety of a novel, long-acting, prodrug-type potassium channel opener, Y-27152, in healthy volunteers, *J. Clin. Pharmacol.*, 1996, 36 (5), 439-451.

In one embodiment, the pharmaceutical composition of the present invention comprises a non-toxic pharmaceutically acceptable salt of a multifunctional nitroxide derivative of the general formula I. Suitable pharmaceutically acceptable salts include acid addition salts such as, without being limited to, the mesylate salt; the maleate salt, the fumarate salt, the tartrate salt, the hydrochloride salt, the hydrobromide salt, the esylate salt; the p-toluenesulfonate salt, the benzoate salt, the acetate salt, the phosphate salt, the sulfate salt, the citrate salt, the carbonate salt, and the succinate salt. Additional pharmaceutically acceptable salts include salts of ammonium ($NH_4^+$) or an organic cation derived from an amine of the formula $R_4N^+$, wherein each one of the Rs independently is selected from H, $C_1$-$C_{22}$, preferably $C_1$-$C_6$ alkyl, such as methyl, ethyl, propyl, n-butyl, sec-butyl, isobutyl, tert-butyl, n-pentyl, 2,2-dimethylpropyl, n-hexyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrrolydine, piperidine and morpholine. Furthermore, where the multifunctional nitroxide derivatives of the invention carry an acidic moiety, suitable pharmaceutically acceptable salts thereof may include metal salts such as alkali metal salts, e.g., lithium, sodium or potassium salts, and alkaline earth metal salts, e.g., calcium or magnesium salts.

Further pharmaceutically acceptable salts include salts of a cationic lipid or a mixture of cationic lipids. Cationic lipids are often mixed with neutral lipids prior to use as delivery agents. Neutral lipids include, but are not limited to, lecithins; phosphatidylethanolamine; diacyl phosphatidylethanolamines such as dioleoyl phosphatidylethanolamine, dipalmitoyl phosphatidylethanolamine, palmitoyloleoyl phosphatidylethanolamine and distearoyl phosphatidylethanolamine; phosphatidylcholine; diacyl phosphatidylcholines such as dioleoyl phosphatidylcholine, dipalmitoyl phosphatidylcholine, palmitoyloleoyl phosphatidylcholine and distearoyl phosphatidylcholine; phosphatidylglycerol; diacyl phosphatidylglycerols such as dioleoyl phosphatidylglycerol, dipalmitoyl phosphatidylglycerol and distearoyl phosphatidylglycerol; phosphatidylserine; diacyl phosphatidylserines such as dioleoyl- or dipalmitoyl phosphatidylserine; and diphosphatidylglycerols; fatty acid esters; glycerol esters; sphingolipids; cardiolipin; cerebrosides; ceramides; and mixtures thereof. Neutral lipids also include cholesterol and other 3β hydroxy-sterols.

Examples of cationic lipid compounds include, without being limited to, Lipofectin® (Life Technologies, Burlington, Ontario) (1:1 (w/w) formulation of the cationic lipid N-[1-(2,3-dioleyloxy)propyl]-N,N,N-trimethylammonium chloride and dioleoylphosphatidyl-ethanolamine); Lipofectamine™ (Life Technologies, Burlington, Ontario) (3:1 (w/w) formulation of polycationic lipid 2,3-dioleyloxy-N-[2(spermine-carboxamido)ethyl]-N,N-dimethyl-1-propanamin-iumtrifluoroacetate and dioleoylphosphatidyl-ethanolamine), Lipofectamine Plus (Life Technologies, Burlington, Ontario) (Lipofectamine and Plus reagent), Lipofectamine 2000 (Life Technologies, Burlington, Ontario) (Cationic lipid), Effectene (Qiagen, Mississauga, Ontario) (Non liposomal lipid formulation), Metafectene (Biontex, Munich, Germany) (Polycationic lipid), Eu-fectins (Promega Biosciences, San Luis Obispo, Calif.) (ethanolic cationic lipids numbers 1 through 12: $C_{52}H_{106}N_6O_4 \cdot 4CF_3CO_2H$, $C_{88}H_{178}N_8O_4S_2 \cdot 4CF_3CO_2H$, $C_{40}H_{84}NO_3P \cdot CF_3CO_2H$, $C_{50}H_{103}N_7O_3 \cdot 4CF_3CO_2H$, $C_{55}H_{116}N_8O_2 \cdot 6CF_3CO_2H$, $C_{49}H_{102}N_6O_3 \cdot 4CF_3CO_2H$, $C_{44}H_{89}N_5O_3 \cdot 2CF_3CO_2H$, $C_{100}H_{206}N_{12}O_4S_2 \cdot 8CF_3CO_2H$, $C_{162}H_{330}N_{22}O_9 \cdot 13CF_3CO_2H$, $C_{43}H_{88}N_4O_2 \cdot 2CF_3CO_2H$, $C_{43}H_{88}N_4O_3 \cdot 2CF_3CO_2H$, $C_{41}H_{78}NO_8P$); Cytofectene (Bio-Rad, Hercules, Calif.) (mixture of a cationic lipid and a neutral lipid), GenePORTER® (Gene Therapy Systems, San Diego, Calif.) (formulation of a neutral lipid (Dope) and a cationic lipid) and FuGENE 6 (Roche Molecular Biochemicals, Indianapolis, Ind.) (Multi-component lipid based non-liposomal reagent).

The pharmaceutically acceptable salts of the present invention may be formed by conventional means, e.g., by reacting the free base form of the active agent, i.e., the multifunctional nitroxide derivative of the invention, with one or more equivalents of the appropriate acid in a solvent or medium in which the salt is insoluble, or in a solvent such as water which is removed in vacuo or by freeze drying, or by exchanging the anion/cation on a suitable ion exchange resin.

In one embodiment, the pharmaceutical composition of the present invention is formulated as nanoparticles.

The pharmaceutical compositions provided by the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent, e.g., the multifunctional nitroxide derivative of the invention, into association with a liquid carrier, a finely divided solid carrier, or both, and then, if necessary, shaping the product into the desired formulation. The compositions may be in solid, semisolid or liquid form and may further include pharmaceutically acceptable fillers, carriers, diluents or adjuvants, and other inert ingredients and excipients. The compositions can be formulated for any suitable route of administration, e.g., oral, nasogastric, nasoenteric, orogastric, parenteral (e.g., intramuscular, subcutaneous, intraperitoneal, intravenous, intraarterial or subcutaneous injection, or implant), gavage, buccal, nasal, sublingual or topical administration, as well as for inhalation. The dosage will depend on the state of the patient, and will be determined as deemed appropriate by the practitioner.

The pharmaceutical composition of the present invention may be in a form suitable for oral use, e.g., as tablets, troches, lozenges, aqueous, or oily suspensions, dispersible powders or granules, emulsions, hard or soft capsules, or syrups or elixirs. Compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for control release. The pharmaceutical composition of the invention may also be in the form of oil-in-water emulsion.

The pharmaceutical composition of the present invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution and isotonic sodium chloride solution.

The pharmaceutical compositions of the invention may be in any suitable form, e.g., tablets such as matrix tablets, in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity.

The pharmaceutical compositions of the present invention may comprise the active agent formulated for controlled release in microencapsulated dosage form, in which small droplets of the active agent are surrounded by a coating or a membrane to form particles in the range of a few micrometers to a few millimeters, or in controlled-release matrix.

Another contemplated formulation is depot systems, based on biodegradable polymers, wherein as the polymer degrades, the active agent is slowly released. The most common class of biodegradable polymers is the hydrolytically labile polyesters prepared from lactic acid, glycolic acid, or combinations of these two molecules. Polymers prepared from these individual monomers include poly(D, L-lactide) (PLA), poly(glycolide) (PGA), and the copolymer poly(D,L-lactide-co-glycolide) (PLG).

Pharmaceutical compositions according to the present invention, when formulated for inhalation, may be administered utilizing any suitable device known in the art, such as metered dose inhalers, liquid nebulizers, dry powder inhalers, sprayers, thermal vaporizers, electrohydrodynamic aerosolizers, and the like.

The multifunctional nitroxide derivatives and pharmaceutical compositions of the invention are useful for treating, preventing and/or managing diseases, disorders or conditions associated with high levels of reactive oxygen species (ROS), i.e., oxidative stress, or endothelial dysfunction.

In one embodiment, said disease, disorder or condition associated with oxidative stress or endothelial dysfunction is a disease, disorder or condition associated with ischemia-reperfusion injury. Non-limiting examples of such diseases include sepsis, septic shock, stroke, cataract formation, glaucoma, geographic atrophy, macular degeneration, angina, hemorrhagic shock, superantigen-induced circulatory shock, renal reperfusion injury, contrast agent-induced nephropathy, retinopathy of prematurity, necrotizing enterocolitis, neonatal respiratory distress syndrome, lung ischemia reperfusion injury, e.g., following transplantation, complications of IL-2 biotherapy, myocardial infarction, complications of cardiopulmonary bypass surgery, limb reperfusion injury, post-prostatectomy related erectile dysfunction, reperfusion complications related to vascular surgery including carotid endarterectomy, aortic aneurysm repair, peripheral arterial embolectomy and thrombectomy, crush injury, compartment syndrome, organ preservation, head trauma, and spinal cord injury.

In another embodiment, said disease, disorder or condition associated with oxidative stress or endothelial dysfunction is a neurodegenerative disease such as, without being limited to, Parkinson's disease, Alzheimer's disease, and amyotrophic lateral sclerosis.

In a further embodiment, said disease, disorder or condition associated with oxidative stress or endothelial dysfunction is an inflammatory or immune disease. In certain particular embodiments, said inflammatory or immune diseases is selected from sepsis, uveitis, rheumatoid arthritis, rheumatoid spondylitis, osteoarthritis, inflamed joints, eczema, inflammatory skin conditions, inflammatory eye conditions, conjunctivitis, tissue necrosis resulting from inflammation, tissue rejection following transplant surgery, graft vs. host disease, Crohn's disease and ulcerative colitis, airway inflammation, asthma, bronchitis, systemic lupus erythematosis, multiple sclerosis, glaucoma, smoking-induced lung injury, pulmonary fibrosis, pancreatitis, cardiomyopathy including chemotherapy-induced cardiomyopathy, complications of IL-2 biotherapy, diabetes, diabetic complications including diabetic retinopathy, peripheral neuropathy, acute macular degeneration, skin ulcers, renal disease, neumonia, mucositis, adult respiratory distress syndrome, smoke inhalation, or cutaneous burn injury. In other particular embodiments, said inflammatory disease is an inflammatory disease of the lung caused by inhalation of toxic agents or irritants such as chlorine, phosgene, and smoke.

In still another embodiment, said disease, disorder or condition associated with oxidative stress or endothelial dysfunction is cancer or a condition associated with chemotherapy or radiation treatment of cancer.

In a further aspect, the present invention thus provides a multifunctional nitroxide derivative of the general formula I as defined above, or an enantiomer, diastereomer, racemate, or a pharmaceutically acceptable salt, solvate or prodrug thereof, for use in treatment of a disease, disorder or condition associated with oxidative stress or endothelial dysfunction.

In still another aspect, the present invention provides a method for treatment of a disease, disorder or condition associated with oxidative stress or endothelial dysfunction, said method comprising administering to an individual in need a therapeutically effective amount of a multifunctional nitroxide derivative of the general formula I as defined above, or an enantiomer, diastereomer, racemate, or a pharmaceutically acceptable salt, solvate or prodrug thereof.

The invention will now be illustrated by the following non-limiting Examples.

EXAMPLES

Example 1

Synthesis of Compound 2

As generally depicted in Scheme 1, a mixture of 3-isothiocyanatopyridine (1.735 g) and 3-amino-2,2,5,5-tetramethylpyrrolidin-nitroxide (2.0 g) in methylene chloride (30 ml) was stirred at room temperature for 8 hr. Thin layer chromatography (TLC) showed some unreacted starting material. The reaction mixture was stirred overnight at room temperature, and it was then concentrated on rotavap. The residue, 1-(pyridin-3-yl)-3-(2,2,5,5-tetramethylpyrrolidin-nitroxide-3-yl)thiourea (3.730 g) obtained was used for further reaction.

A mixture of 1-(pyridin-3-yl)-3-(2,2,5,5-tetramethylpyrrolidin-nitroxide-3-yl)thiourea (3.6 g), cyanamide (5.125 g), 1-(3-dimethylaminopropyl)-3-ethylcarbodiimide hydrochloride (EDCI) (2.805 g) and triethylamine (4.928 g) in acetonitrile (50 ml) was stirred at room temperature for 24 hr, and the mixture was then refluxed at 80° C. for 4 hr. The reaction mixture was concentrated on rotavap and purified on silica gel column using methanol-methylene chloride (5-10%) to provide the oxy radical of 2-cyano-1-(1-hydroxy-2,2,5,5-tetramethylpyrrolidin-3-yl)-3-(pyridin-3-yl) guanidine, 2 (3.050 g). MS (CI+) m/z 301.17 (M+1, 302.18).

Scheme 1: General procedure for the synthesis of nitroxide derivatives such as compounds 2, $5_b$, $25_{a-c}$, 29 and $35_{a-c}$

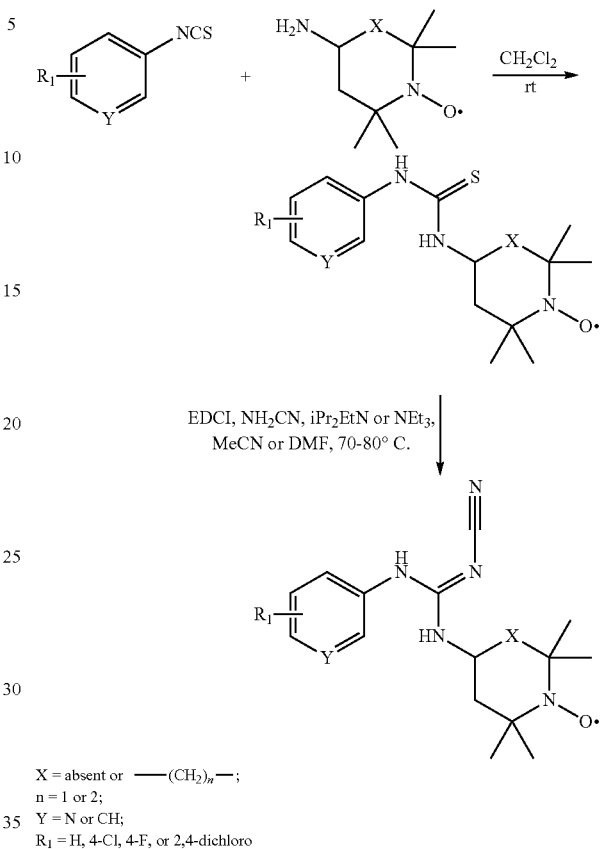

X = absent or ——$(CH_2)_n$——;
n = 1 or 2;
Y = N or CH;
$R_1$ = H, 4-Cl, 4-F, or 2,4-dichloro Example 2

Synthesis of Compound 3

The synthesis of the oxy radical of 2-cyano-1-(1-hydroxy-2,2,5,5-tetramethylpyrrolidin-3-yl)-3-(pyridin-4-yl)guanidine, 3, commences with the preparation of thiourea from the reaction of 4-isothiocyanatopyridine and 3-amino-2,2,5,5-tetramethylpyrrolidin-1-nitroxide. The 1-(pyridin-4-yl)-3-(2,2,5,5-tetra methylpyrrolidin-nitroxide-3-yl)thiourea obtained is then reacted with cyanamide, EDCI and diisopropylethylamine in DMF, under the same conditions described in Example 1, to yield the desired cyanoguanidine product.

Example 3

Synthesis of Compound $5_b$

As generally depicted in Scheme 1, a mixture of (3-amino-2,2,5,5-tetramethylpyrrolidin-1-yl)oxidanyl (1.580 g, 0.01 mol) and 6-chloro-3-pyridyl isothiocyanate (1.706 g, 0.01 mol) in methylene chloride (20 ml) was stirred at room temperature for 24 hr. The reaction mixture was concentrated on rotary evaporator. The residue obtained after concentration was purified on silica gel column using 5% methanol-methylene chloride to give the (3-{[(6-chloropyridin-3-yl)carbamothioyl]amino}-2,2,5,5-tetramethyl-pyrrolidin-1-yl)oxidanyl as an yellow colored oil (3.130 g).

A mixture of (3-{[(6-chloropyridin-3-yl)carbamothioyl] amino}-2,2,5,5-tetramethylpyrrolidin-1-yl)oxidanyl (2.825 g, 0.0086 mol), cyanamide (3.612 g, 0.086 mol), EDCI (2.465 g, 0.0129 mol) and triethylamine (4.81 ml, 0.034 mol) in acetonitrile (40 ml) was refluxed at 80° C. for 2 days. The reaction mixture was concentrated and the residue was purified on silica gel column using 5% methanol-methylene chloride to provide the oxy radical of 2-cyano-1-(6-chloropyridin-3-yl)-3-(1-hydroxy-2,2,5,5-tetramethylpyrrolidin-3-yl) guanidine, $5_b$, as pale yellow colored solid (1.8 g). MS (ES) m/z 335.14 (M+1, 336.2).

Example 4

Synthesis of Compound $25_a$

As generally depicted in Scheme 1, a mixture of (3-amino-2,2,5,5-tetramethylpyrrolidin-1-yl)oxidanyl (0.532 g, 0.0033 mol) and 4-fluorophenyl isothiocyanate (0.408 ml, 0.0033 mol) in methylene chloride (20 ml) was stirred at room temperature for 3 hr. The reaction mixture was concentrated on rotary evaporator, and the residue obtained after concentration was suspended in hexane. The liquid was removed and the solid was dried under vacuum to give the {2,2,5,5-tetramethyl-3-[(4-fluorophenyl-1-ylcarbamothioyl)amino]pyrrolidin-1-yl}oxidanyl as an yellow colored solid.

The {2,2,5,5-tetramethyl-3-[(4-fluorophenyl-1-ylcarbamothioyl)amino]pyrrolidin-1-yl}oxidanyl obtained was combined with cyanamide (1.385 g, 0.033 mol), EDCI (0.945 gm, 0.0049 mol) and triethylamine (1.850 ml, 0.012 mol) in acetonitrile (25 ml), and was stirred at 80° C. for 24 hr. The reaction mixture was concentrated and the residue was diluted with ethyl acetate and water (25 ml each). The organic later was collected and concentrated on rotary evaporator. The crude product was then purified on silica gel column using 40-50% ethyl acetate-hexane to provide the oxy radical of 2-cyano-1-(4-fluorophenyl)-3-(1-hydroxy-2,2,5,5-tetramethylpyrrolidin-3-yl)guanidine, $25_a$ (0.355 gm). MS (ES) m/z 318.17 (M+1, 319.34).

Example 5

Synthesis of Compound $25_b$

As generally depicted in Scheme 1, a mixture of (3-amino-2,2,5,5-tetramethylpyrrolidin-1-yl)oxidanyl (0.500 g, 0.0031 mol) and 4-chlorophenyl isothiocyanate (0.538 g, 0.0031 mol) in methylene chloride (25 ml) was stirred at room temperature for 6 hr. The reaction mixture was concentrated on rotary evaporator, and the residue obtained after concentration was suspended in hexane. The liquid was removed and the solid was dried under vacuum to give the {2,2,5,5-tetramethyl-3-[(4-chlorophenyl-1-ylcarbamothioyl)amino]pyrrolidin-1-yl}oxidanyl as an yellow colored solid.

The {2,2,5,5-tetramethyl-3-[(4-chlorophenyl-1-ylcarbamothioyl)amino]pyrrolidin-1-yl}oxidanyl obtained was combined with cyanamide (1.3 g, 0.031 mol), EDCI (0.710 g, 0.0037 mol) and triethylamine (1.250 g, 0.012 mol) in acetonitrile (30 ml) and was stirred at 80° C. for 24 hr. The reaction mixture was concentrated and the residue was diluted with ethyl acetate and water (25 ml each). The organic later was collected and concentrated on rotary evaporator. The crude product was then purified on silica gel column using 40% ethyl acetate-hexane to provide the oxy radical of 2-cyano-1-(4-chlorophenyl)-3-(1-hydroxy-2,2,5, 5-tetramethylpyrrolidin-3-yl)guanidine, $25_b$ (0.175 g). MS (ES⁺) m/z 334.13 (M+1, 335.25).

Example 6

Synthesis of Compound $25_c$

As generally depicted in Scheme 1, a mixture of (3-amino-2,2,5,5-tetramethylpyrrolidin-1-yl)oxidanyl (0.450 mg, 0.0028 mol) and 4-bromophenyl isothiocyanate (0.615 g, 0.0028 mol) in methylene chloride (30 ml) was stirred at room temperature for 4 hr. The reaction mixture was concentrated on rotary evaporator, and the residue obtained after concentration was suspended in hexane. The liquid was removed and the solid was dried under vacuum to give the {2,2,5,5-tetramethyl-3-[(4-bromophenyl-1-ylcarbamothioyl)amino]pyrrolidin-1-yl}oxidanyl as an yellow colored solid.

The {2,2,5,5-tetramethyl-3-[(4-bromophenyl-1-ylcarbamothioyl)amino]pyrrolidin-1-yl}oxidanyl obtained was combined with cyanamide (0.028 mol), EDCI (0.0042 mol) and triethylamine (0.011 mol) in acetonitrile (25 ml), and was stirred at 70° C. for 24 hr. The reaction mixture was concentrated and the residue was diluted with ethyl acetate and water (25 ml each). The organic later was collected and concentrated on rotary evaporator. The crude product was then purified on silica gel column using 40-100% ethyl acetate-hexane to provide the oxy radical of 2-cyano-1-(4-bromophenyl)-3-(1-hydroxy-2,2,5,5-tetramethylpyrrolidin-3-yl)guanidine, 25, (0.280 gm). MS (ES⁺) m/z 378.10 (M+1, 379.22).

Example 7

Synthesis of Compound 29

As generally depicted in Scheme 1, a mixture of (3-amino-2,2,5,5-tetramethylpyrrolidin-1-yl)oxidanyl (0.500 g, 0.0031 mol) and 2,4-dichlorophenyl isothiocyanate (0.0034 mol) in methylene chloride (25 ml) was stirred at room temperature for 6 hr. The reaction mixture was concentrated on rotary evaporator, and the residue obtained after concentration was suspended in hexane. The liquid was removed and the solid was dried under vacuum to give the {2,2,5,5-tetramethyl-3-[(2,4-dichlorophenyl-1-ylcarbamothioyl)amino]pyrrolidin-1-yl}oxidanyl as an yellow colored solid.

The {2,2,5,5-tetramethyl-3-[(2,4-dichlorophenyl-1-ylcarbamothioyl)amino]pyrrolidin-1-yl}oxidanyl obtained was combined with cyanamide (1.3 g, 0.031 mol), EDCI (0.710 g, 0.0037 mol) and triethylamine (1.250 g, 0.012 mol) in acetonitrile (30 ml) and was stirred at 80° C. for 24 hr. The reaction mixture was concentrated and the residue was diluted with ethyl acetate and water (25 ml each). The organic later was collected and concentrated on rotary evaporator. The crude product was then purified on silica gel column using 5% methanol-methylene chloride to provide the oxy radical of 2-cyano-1-(2,4-dichlorophenyl)-3-(1-hydroxy-2,2,5,5-tetramethylpyrrolidin-3-yl)guanidine, 29 (0.705 gm). MS (ES⁺) m/z 368.06 (M+1, 379.23).

Example 8

Synthesis of Compound $35_a$

As generally depicted in Scheme 1, a mixture of (4-amino-2,2,6,6-tetramethylpiperidin-1-yl)oxidanyl (0.500 g, 0.0029 mol) and 4-fluorophenyl isothiocyanate (0.0029 mol) in methylene chloride (20 ml) was stirred at room temperature for overnight. The reaction mixture was concentrated on rotary evaporator. The residue obtained after concentration was dried under vacuum to give the {2,2,6,6-tetramethyl-3-[(4-fluorophenyl-1-ylcarbamothioyl)amino]piperidin-1-yl}oxidanyl as a pale yellow colored solid.

The {2,2,6,6-tetramethyl-3-[(4-fluorophenyl-1-ylcarbamothioyl)amino]piperidin-1-yl}oxidanyl obtained was combined with cyanamide (1.220 g, 0.029 mol), EDCI (0.840 g, 0.0043 mol) and triethylamine (1.620 ml, 0.011 mol) in acetonitrile (20 ml) and was stirred at 70° C. for 4 hr. The reaction mixture was concentrated and the residue was diluted with ethyl acetate and water (25 ml each). The organic later was collected and concentrated on rotary evaporator. The crude product was then purified on silica gel column using 10% methanol-methylene chloride to provide the oxy radical of 2-cyano-1-(4-fluorophenyl)-3-(1-hydroxy-2,2,6,6-tetramethyl piperidin-4-yl)guanidine, $35_a$ (0.248 g). MS (ES) m/z 332.19 (M+1, 333.4).

Example 9

Synthesis of Compound $35_b$

As generally depicted in Scheme 1, a mixture of (4-amino-2,2,6,6-tetramethylpiperidin-1-yl)oxidanyl (0.500 g, 0.0029 mol) and 4-chlorophenyl isothiocyanate (0.490 g, 0.0029 mol) in methylene chloride (20 ml) was stirred at room temperature for overnight. The reaction mixture was concentrated on rotary evaporator. The residue obtained after concentration was dried under vacuum to give the {2,2,6,6-tetramethyl-3-[(4-chlorophenyl-1-ylcarbamothioyl)amino]piperidin-1-yl}oxidanyl as a pale yellow colored solid.

The {2,2,6,6-tetramethyl-3-[(4-chlorophenyl-1-ylcarbamothioyl)amino]piperidin-1-yl}oxidanyl obtained was combined with cyanamide (1.220 g, 0.029 mol), EDCI (0.840 g, 0.0043 mol) and triethylamine (1.620 ml, 0.011 mol) in acetonitrile (20 ml) and was stirred at 80° C. for 24 hr. The reaction mixture was concentrated and the residue was diluted with ethyl acetate and water (25 ml each). The organic later was collected and concentrated on rotary evaporator. The crude product was then purified on silica gel column using 10% methanol-methylene chloride to provide the oxy radical of 2-cyano-1-(4-chlorophenyl)-3-(1-hydroxy-2,2,6,6-tetra methylpiperidin-4-yl)guanidine, $35_b$ (0.415 g). MS (ES) m/z 348.1 (M+1, 339.30).

Example 10

Synthesis of Compound $35_c$

As generally depicted in Scheme 3, a mixture of (4-amino-2,2,6,6-tetramethylpiperidin-1-yl)oxidanyl (0.600 g, 0.0035 mol) and 4-bromophenyl isothiocyanate (0.0035 mol) in methylene chloride (30 ml) was stirred at room temperature for 3 hr. The reaction mixture was concentrated on rotary evaporator and suspended in ethyl acetate and hexane (10 ml each). The solid was filtered and dried under vacuum to give the {2,2,6,6-tetramethyl-3-[(4-bromophenyl-1-ylcarbamothioyl)amino]piperidin-1-yl}oxidanyl as a pale yellow colored solid.

The {2,2,6,6-tetramethyl-3-[(4-bromophenyl-1-ylcarbamothioyl)amino]piperidin-1-yl}oxidanyl obtained was combined with cyanamide (1.470 g, 0.035 mol), EDCI (1.0 g, 0.0052 mol) and triethylamine (2.00 ml, 0.014 mol) in acetonitrile (20 ml) and was stirred at 75° C. for 7 hr. The reaction mixture was concentrated and the residue was diluted with ethyl acetate and water (25 ml each). The organic later was collected and concentrated on rotary evaporator. The crude product was then purified on silica gel column using 50-100% ethyl acetate-hexane to provide the oxy radical of 2-cyano-1-(4-bromophenyl)-3-(1-hydroxy-2,2,6,6-tetramethylpiperidin-4-yl)guanidine, 35, (0.240 g). MS (ES$^+$) m/z 392.24 (M+1, 393.26).

Example 11

Compound 2 Reduces Infarct Size and Myocardial Damage in a Rat Model of Myocardial Ischemia-Reperfusion Injury (MIRI)

Male adult Wistar rats (250-300 g), anesthetized with thiopentone sodium and mechanically ventilated [fraction of inspired oxygen (FiO$_2$)=30%; intermittent mandatory ventilation (IMV)=70 bpm, tidal volume (TV)=8-10 ml/kg], underwent placement of a ligature around the left anterior descending (LAD) coronary artery approximately 1-2 mm below its origin. Ischemia was induced by tightening the threads of the coronary suture and was maintained for 20 min. Reperfusion for 2 hours was obtained by reopening the chest and cutting the ligature around the coronary artery. Rats were randomly allocated to the following groups (n=10 per experimental arm): (i) MIRI+vehicle group: rats were subjected to coronary artery occlusion (20 min) followed by reperfusion (2 hours); (ii) MIRI+compound 2 group: rats were subjected to the surgical procedures described above and were treated with compound 2 at 1 mg/kg IV bolus followed by a continuous IV infusion of 2 mg/kg/h; and (iii) Sham+vehicle group: rats were subjected to identical surgical procedures, except for coronary artery occlusion, and were kept under anaesthesia for the duration of the experiment. At the end of the 2 hours reperfusion period, the LAD was re-occluded, and 1 ml of Evans blue dye (2% wt/vol) was injected to the animal via the jugular vein. The area at risk (AAR), i.e., the non-perfused and thus non-stained myocardium, was separated from the non-ischemic (blue) tissue and expressed as a percentage of the left ventricle. The tissue from the AAR staining with p-Nitroblue tetrazolium was separated from the infarcted tissue and weighed, and the infarct size was expressed as a percentage of the AAR. Compound 2 did not produce systemic hypotension in rats subjected to MIRI, as shown in FIG. 1. This was significant because systemic hypotension would severely compromise and exacerbate regional coronary ischemia.

Figure 2A:
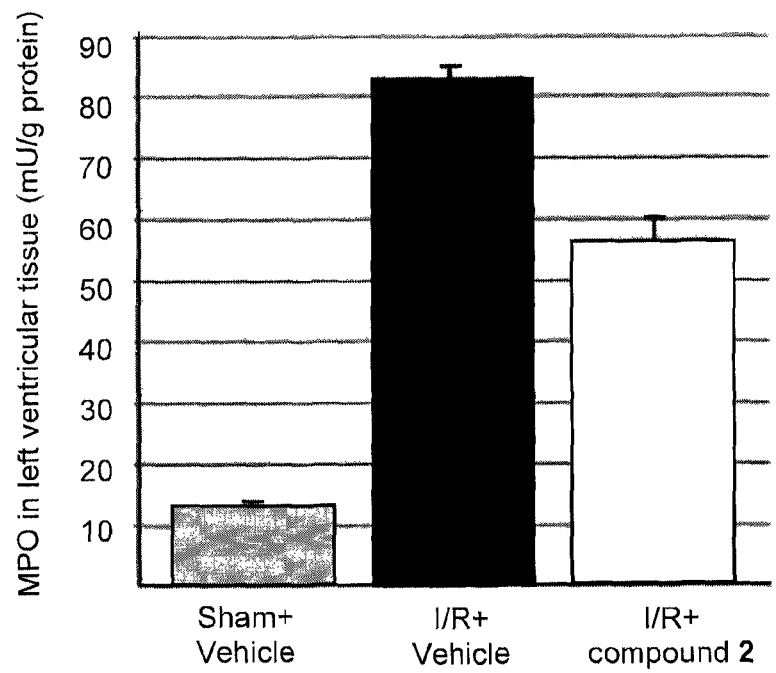
FIGS. 2A-2B demonstrate the histological protection afforded by compound 2 in a rat model of MIRI described in Example 11, indicating that compound 2, when administered prior to reperfusion at 1 mg/kg IV bolus followed by a continuous IV infusion of 2 mg/kg/h, significantly reduced both myocardial myeloperoxidase (MPO) (2A) and tissue infarction (2B) ($p<0.01$ vs. I/R+vehicle; n=10 rats per group). The results were analyzed by one-way ANOVA followed by a Bonferroni post-hoc test for multiple comparisons. All values and text are expressed as mean±standard error of the mean (SEM) of N number of animals.
Figure 2B:
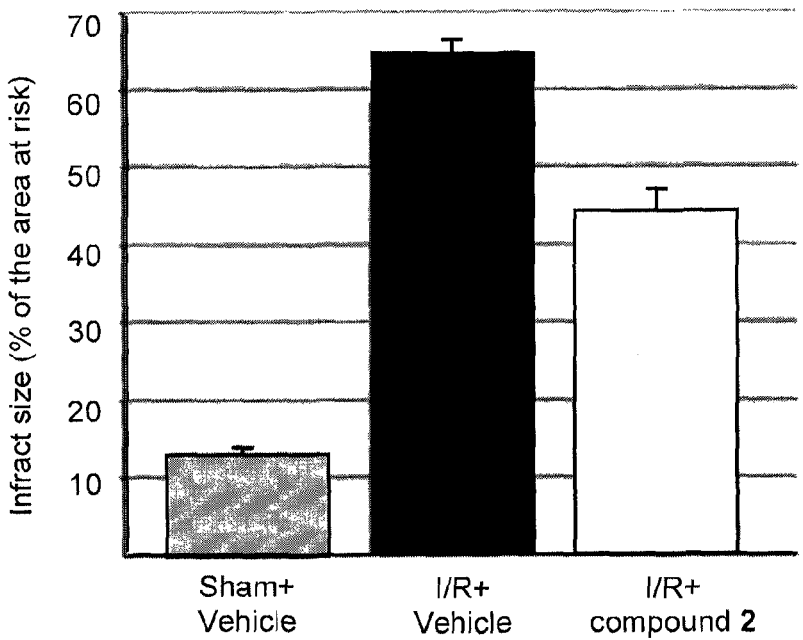

As shown in FIGS. 2A-2B, compound 2 significantly reduced both myocardial myeloperoxidase (MPO) (2A) and tissue infarction (2B).

Figure 3A:
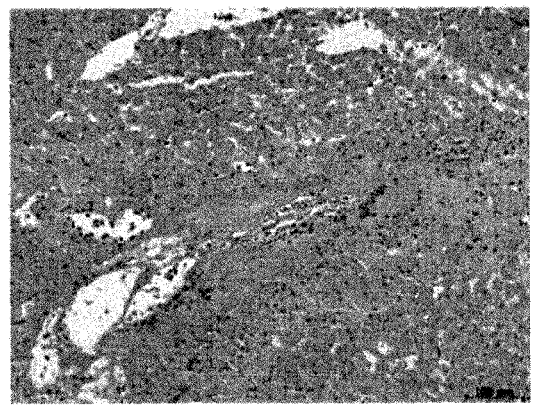
FIGS. 3A-3C illustrates the histological effects of MIRI, i.e., severe myocyte necrosis, edema and neutrophil infiltration, in rats subjected to coronary artery occlusion (20 min) followed by reperfusion (2 hours) as described in Example 11 (3A); sham controls, i.e., rats subjected to identical surgical procedures except for coronary artery occlusion (3B); and rats subjected to identical surgical procedures and treated with compound 2, prior to reperfusion at 1 mg/kg IV bolus followed by a continuous IV infusion of 2 mg/kg/h (3C). As shown, compound 2 profoundly attenuated virtually all histologic features of injury induced by MIRI.
Figure 3B:
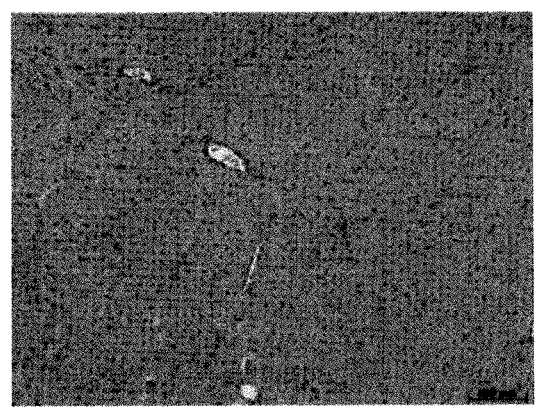
Figure 3C:
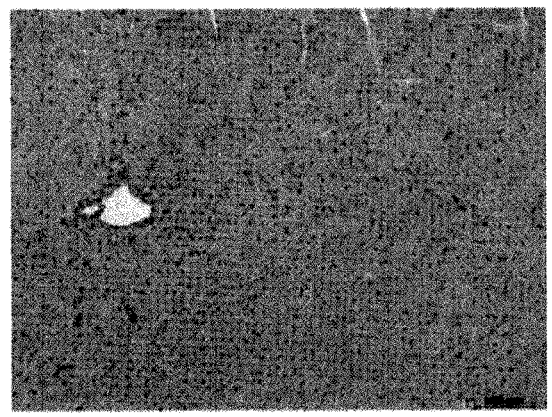

As further shown in FIGS. 3A-3C, while MIRI induced severe myocyte necrosis, edema and neutrophil infiltration (3A) compared to a sham control (3B), administration of compound 2 prior to reperfusion profoundly attenuated virtually all histologic features of injury (3C).

In an ex vivo rat vascular ring system precontracted with norepinephrine (1 μM), compound 2 (100 μM) was found to be a less potent ex vivo vasodilator compared to pinacidil, having ED$_{50}$ that is one log greater than that of pinacidil, indicative of a loss in sarcolemmal K$^+$-ATP channel activation.

Example 12

Figure 4A:
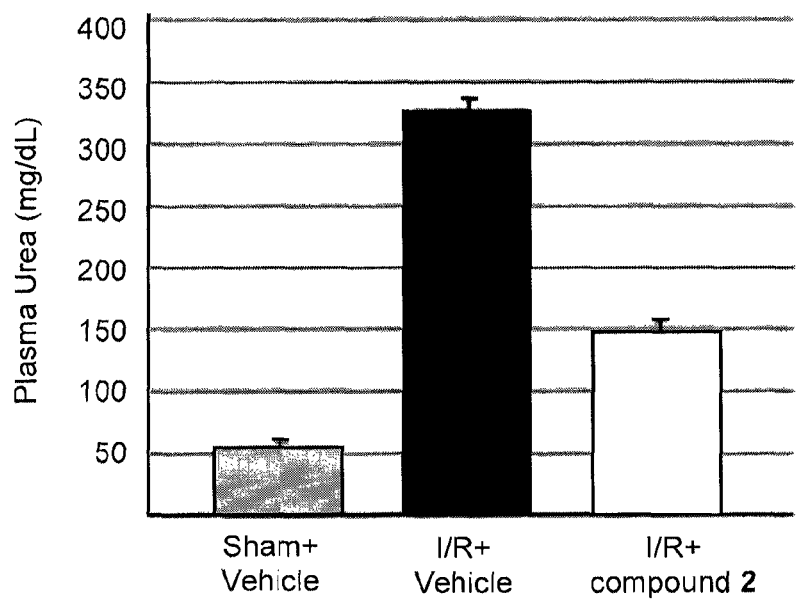
FIGS. 4A-4C show that addition of compound 2 before reperfusion in a murine model of renal ischemia-reperfusion injury described in Example 12 profoundly attenuated elevations in plasma blood urea nitrogen (BUN) and creatinine (4A and 4B, respectively), as well as in renal meyloperoxidase (MPO) (4C) ($p<0.01$ vs. vehicle control).
Figure 4B:
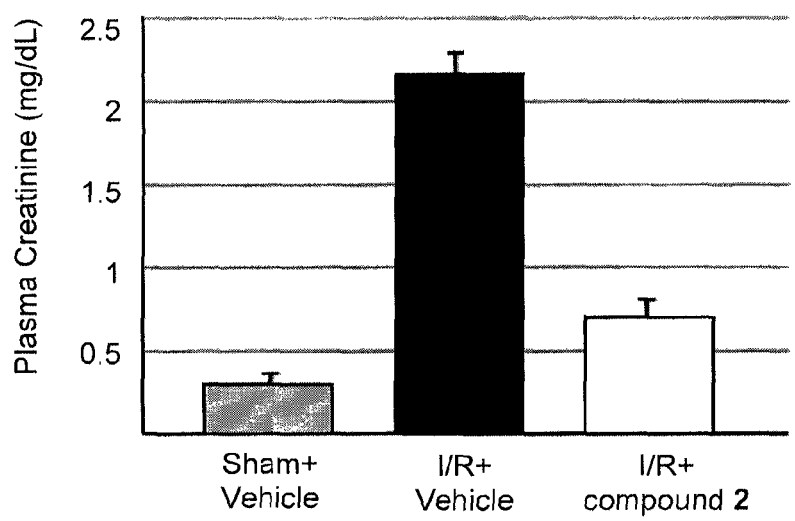
Figure 4C:
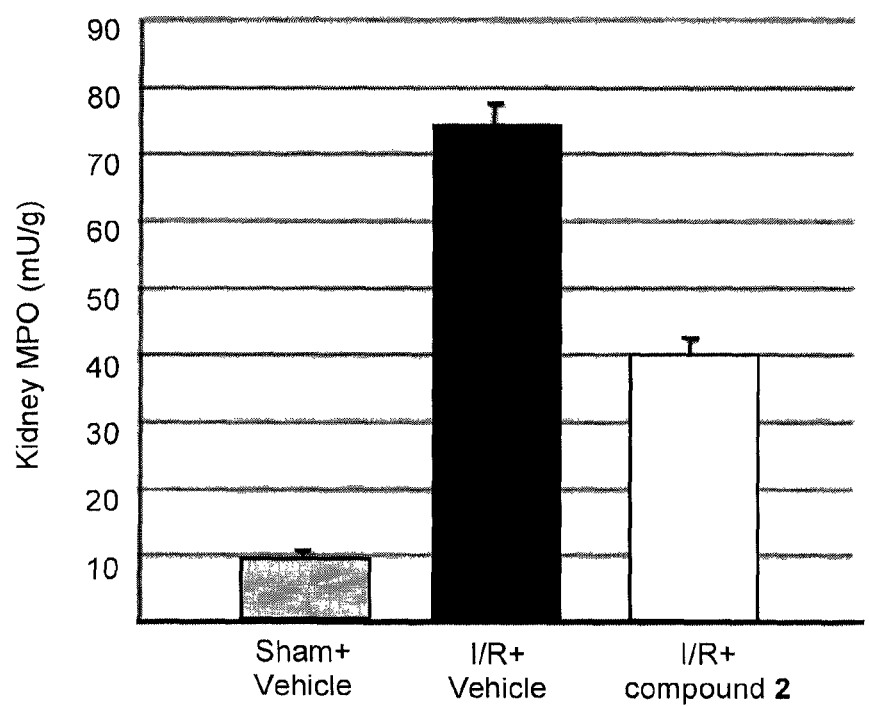

Compound 2 is Protective in a Murine Model of Renal Ischemia-Reperfusion Injury Anesthetized male CD mice underwent bilateral clamping of the renal pedicles for 30 minutes, followed by 6 hours of reperfusion. As shown in FIGS. 4A-4C, addition of compound 2 before reperfusion profoundly attenuated elevations in plasma blood urea nitrogen (BUN) and creatinine (4A and 4B, respectively), and in renal meyloperoxidase (MPO), a marker of neutrophil infiltration (4C) (p<0.01 vs. vehicle control). Histologic studies (not shown) revealed that compound 2 provided near total protection against severe renal tubular necrosis.

Example 13

Figure 5A:
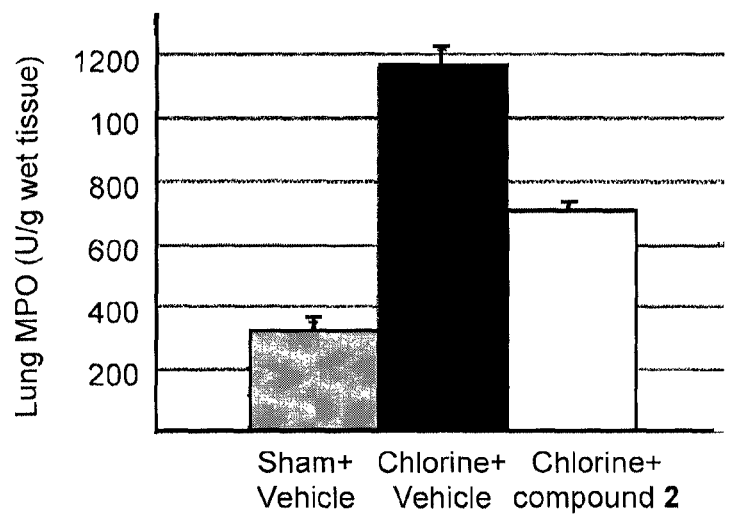
FIGS. 5A-5B show that IP administration of compound 2 (30 mg/kg/dose in 0.5 ml D5W) following chlorine exposure, in a murine model of acute chlorine inhalation injury (CILI), reduced the elevation in MPO (5A), indicating polymorphonuclear leukocytes (PMN) infiltration, and histologic lung damage (5B) in male Balb/c mice by 52% ($p<0.0001$) and 43% ($p<0.001$), respectively, relatively to placebo (D5W).
Figure 5B:
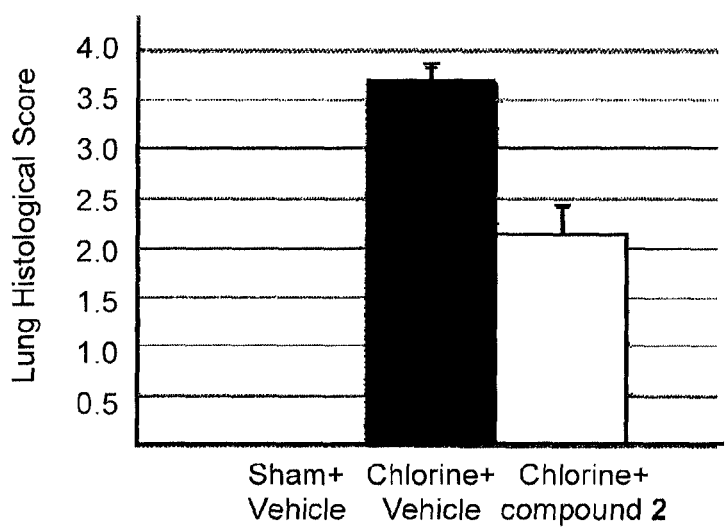

Compound 2 is Effective as a Rescue Therapy in a Murine Model of Acute Chlorine Inhalation Injury Male Balb/c mice (25 g; n=6 per experimental group) were exposed in a closed environmental chamber to 400 ppm $Cl_2$ in air for 30 min. 15 min after the conclusion of $Cl_2$ exposure, mice were initiated on a q12h regimen of compound 2 (30 mg/kg/dose IP in 0.5 ml dextrose 5% in water [D5W]). At 24 h, mice were euthanized and lung tissue taken for examination of polymorphonuclear leukocytes (PMN) infiltration (as reflected in the level of MPO) and histology, by a pathologist blinded to the experimental arm assignment. As shown in FIGS. 5A-5B, compound 2 therapy reduced the elevation in MPO (5A) and histologic lung damage (5B) by 52% (p<0.0001) and 43% (p<0.001), respectively, relative to placebo (D5W).

Figure 6:
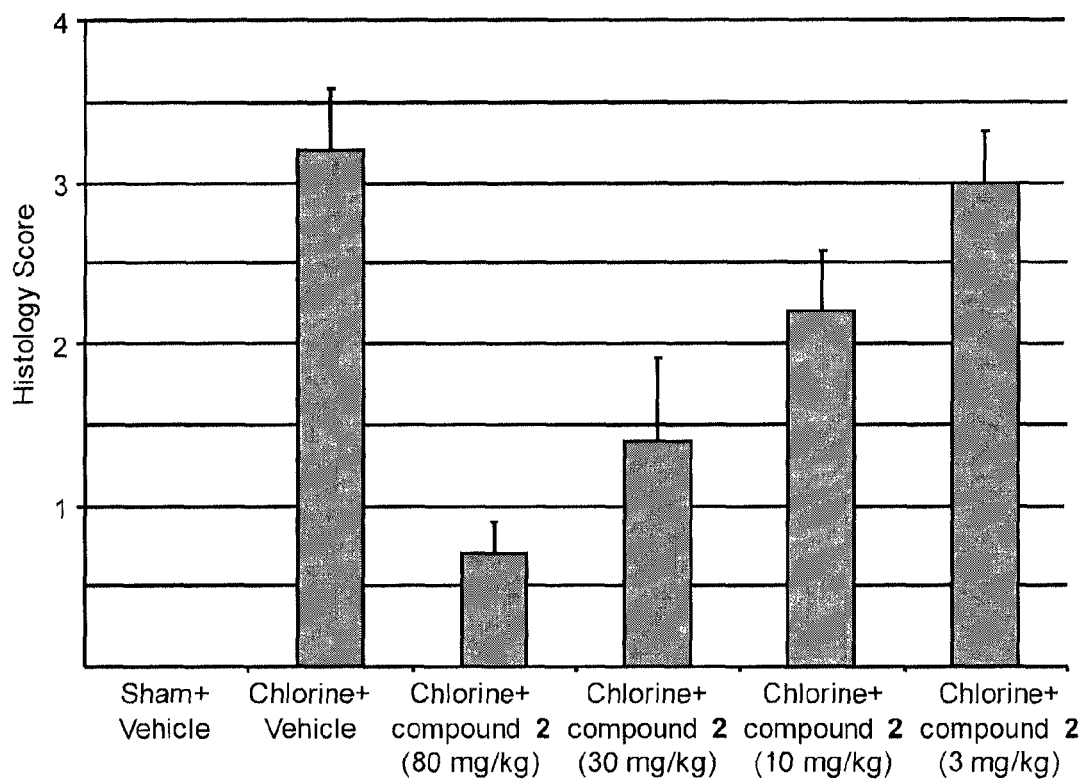
FIG. 6 shows histology scores demonstrating that compound 2, formulated in saline solution and given in 0.25 ml volume, IP, at 2 h and 6 h after $Cl_2$ exposure, attenuated lung injury in a dose-dependent manner, ranging from 3 mg to 80 mg per dose (or 6 mg to 160 mg per day). Values are expressed as mean±standard error of the mean (SEM) of N number of animals. Histology scores are: Sham/vehicle: mean=0 (n=2 mice, score 0, 0); $Cl_2$+vehicle: mean 3.2, SE 0.37 (n=5, scores 2, 3, 3, 4, 4); $Cl_2$+80 mg/kg: 0.70, SE 0.45 (n=5, scores 0, 1, 1, 1, 1.5); $Cl_2$+30 mg/kg: 1.4 SE 0.51 (n=5, scores 0, 1, 1, 2, 3); $Cl_2$+10 mg/kg: 2.2, SE 0.37 (n=5, scores 1, 2, 2, 3, 3); $Cl_2$+3 mg/kg: 3.0, SE 0.32 (n=5, scores 2, 3, 3, 3, 4).

Dose-response evaluations were performed as described above with little modifications. Compound 2 was formulated in saline solution and given in 0.25 ml volume at 2 h and 6 h after $Cl_2$ exposure by IP. As found, compound 2 attenuated lung injury in a dose-dependent manner, ranging from 3 mg to 80 mg per dose (or 6 mg to 160 mg per day), as exemplified by the improved histology scores shown in FIG. 6.

Example 14

Compound 2 does not Affect Blood Glucose Level

Figure 7:
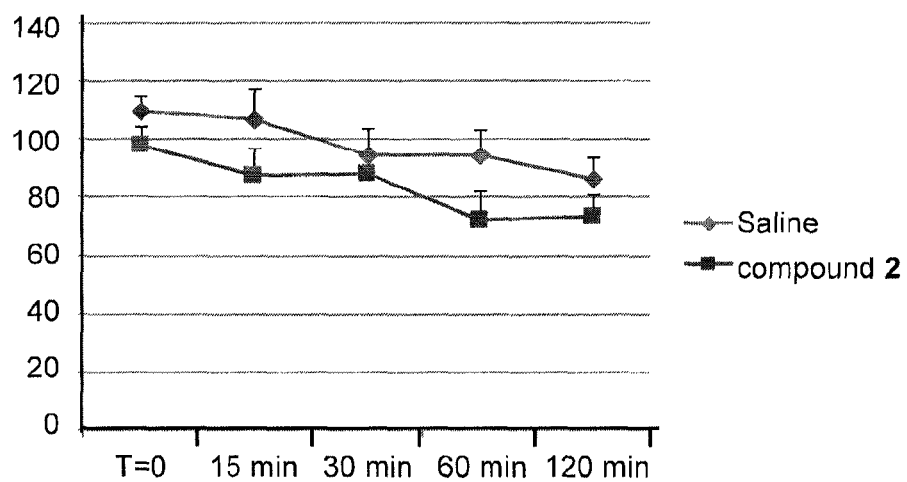
FIG. 7 shows that compound 2, given by IP bolus to male Balb/c mice, did not exhibit any significant effect on blood glucose levels compared with saline vehicle group.

In order to test the effect of compound 2 on blood glucose levels, 0.25 ml of drug formulated in saline solution was given by IP bolus to male Balb/c mice weighing approximately 25 g (n=5). Mice were fasted 4 hr before experiment and remained fast during study period. At indicated time points, 20 μl of blood samples were collected from tail veins under ether anesthesia and glucose levels were measured by using glucometer. As shown in FIG. 7, compound 2 did not exhibit any significant effect on blood glucose levels compared with saline vehicle group.

What is claimed is:

1. A compound of the formula I:

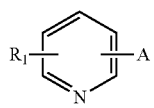

I or an enantiomer, diastereomer, racemate, or a pharmaceutically acceptable salt or solvate thereof,
wherein
A is a moiety of the formula II linked through its terminal —NH group to any carbon atom of the pyridine ring:

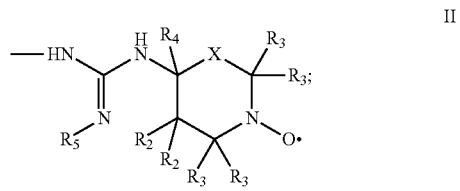

II

X is —$(CR_2R_2)_n$—;
$R_1$ is absent or 1 to 4 substituents each independently selected from the group consisting of halogen, —CN, —OH, —$NO_2$, —$N(R_6)_2$, —$OCF_3$, —$CF_3$, —$OR_6$, —$COR_E$, —$COOR_6$, —$CON(R_6)_2$, —$OCOOR_6$, —$OCON(R_6)_2$, —($C_1$-$C_8$)alkyl, —($C_1$-$C_8$)alkylene-$COOR_6$, —$SR_6$, —$SO_2R_6$, —$SO_2N(R_6)_2$, and —$S(=O)R_6$, wherein said —($C_1$-$C_8$)alkyl and —($C_1$-$C_8$)alkylene-$COOR_6$ may optionally be substituted with —OH, —$OR_3$, —$OCF_3$, —$CF_3$, —$COR_3$, —$COOR_3$, —$OCOOR_3$, —$OCON(R_3)_2$, —($C_1$-$C_8$) alkylene-$COOR_3$, —CN, —$NH_2$, —$NO_2$, —SH, —$SR_3$, —($C_1$-$C_8$)alkyl, —O—($C_1$-$C_8$)alkyl, —$N(R_3)_2$, —$CON(R_3)_2$, —$SO_2R_3$, or —$S(=O)R_3$;
$R_2$ each independently is selected from the group consisting of H, halogen, —$OCF_3$, —$CF_3$, —$OR_7$, —$COR_7$, —$COOR_7$, —$OCOOR_7$, —$OCON(R_7)_2$, —($C_1$-$C_8$) alkylene-$COOR_7$, —CN, —$NO_2$, —SH, —$SR_7$, —($C_1$-$C_8$)alkyl, —$N(R_7)_2$, —$CON(R_7)_2$, —$SO_2R_7$, $SO_2N(R_7)_2$, and —$S(=O)R_7$;
$R_3$ each independently is selected from the group consisting of ($C_1$-$C_8$)alkyl, ($C_2$-$C_8$)alkenyl, and ($C_2$-$C_8$)alkynyl;
$R_4$ is selected from the group consisting of H, —$COOR_7$, —($C_1$-$C_8$)alkylene-$COOR_7$, —CN, —($C_1$-$C_8$)alkyl, and —$CON(R_7)_2$;
$R_5$ is selected from the group consisting of H, —OH, —O—($C_1$-$C_8$)alkyl, —CO—($C_1$-$C_8$)alkyl, —COO—($C_1$-$C_8$)alkyl, —CN, and —$NH_2$;
$R_6$ each independently is selected from the group consisting of H, ($C_1$-$C_8$)alkyl, ($C_3$-$C_{10}$)cycloalkyl, 4-12-membered heterocyclyl, ($C_6$-$C_{14}$)aryl, and —($C_1$-$C_8$)alkylene-$NH_2$;
$R_7$ each independently is selected from the group consisting of H, ($C_1$-$C_8$)alkyl, —($C_1$-$C_8$)alkylene-$NH_2$, ($C_3$-$C_{10}$)cycloalkyl, 4-12-membered heterocyclyl, and ($C_6$-$C_{14}$)aryl, each of which other than H may optionally be substituted with —$OR_6$, —$COR_6$, —$COOR_6$, —$OCOOR_6$, —$OCON(R_6)_2$, —($C_1$-$C_8$)alkylene-$COOR_6$, —CN, —$NO_2$, —$SR_6$, —($C_1$-$C_8$)alkyl, —$N(R_6)_2$, —$CON(R_6)_2$, —$SO_2R_6$, or —$S(=O)R_6$; and
n is an integer of 1 or 2.

2. The compound of claim 1, wherein A is linked to position 2, 3, 4, 5 or 6 of the pyridine ring.

3. The compound of claim 1, wherein
   (i) $R_1$ is absent, or 1, 2, 3, or 4 substituents each independently selected from the group consisting of halogen, —OH, —CN, —$NO_2$, —$N(R_6)_2$, —$OR_6$, —$OCF_3$, —$CF_3$, —$COR_6$, —$COOR_6$, —$CON(R_6)_2$, —$OCOOR_6$, —$OCON(R_6)_2$, —($C_1$-$C_8$)alkyl, —($C_1$-

$C_8$)alkylene-COOR$_6$, —SR$_6$, —SO$_2$R$_6$, —SO$_2$N(R$_6$)$_2$, and —S(=O)R$_6$, wherein R$_6$ each independently is H, (C$_1$-C$_8$)alkyl, or —(C$_1$-C$_8$)alkylene-NH$_2$.

4. The compound of claim 1, wherein (i) R$_2$ is H; or (ii) R$_3$ each independently is (C$_1$-C$_4$)alkyl; or (iii) R$_4$ is H; or (iv) R$_5$ is —CN.

5. The compound of claim 4, wherein R$_3$ are identical.

6. The compound of claim 1, wherein A is linked to position 2, 3, 4, 5 or 6 of the pyridine ring; R$_1$ is absent or 1 to 4 substituents each independently is halogen; X is —(CR$_2$R$_2$)$_n$— wherein n is 1 or 2; R$_2$ is H; R$_3$ each independently is (C$_1$-C$_4$)alkyl; R$_4$ is H; and R$_5$ is —CN.

7. The compound of claim 6, wherein:
(i) X is —(CR$_2$R$_2$)$_n$— wherein n is 1; R$_1$ is absent; R$_3$ is methyl; and A is linked to position 2, 3 or 4 of the pyridine ring, herein identified compounds 8-10, respectively;
(ii) X is —(CR$_2$R$_2$)$_n$— wherein n is 1; R$_1$ is F, Cl or Br, linked to position 6 of the pyridine ring; R$_3$ is methyl; and A is linked to position 2, 3, 4 or 5 of the pyridine ring, herein identified compounds 11$_{a-c}$-14$_{a-c}$, respectively;
(iii) X is —(CR$_2$R$_2$)$_n$— wherein n is 2; R$_1$ is absent; R$_3$ is methyl; and A is linked to position 2, 3 or 4 of the pyridine ring, herein identified compounds 15-17, respectively; or
(iv) X is —(CR$_2$R$_2$)$_n$— wherein n is 2; R$_1$ is F, Cl or Br, linked to position 6 of the pyridine ring; R$_3$ is methyl; and A is linked to position 2, 3, 4 or 5 of the pyridine ring, herein identified compounds 18$_{a-c}$-21$_{a-c}$, respectively.

8. A pharmaceutical composition comprising a compound of claim 1, or an enantiomer, diastereomer, racemate, or a pharmaceutically acceptable salt or solvate thereof, and a pharmaceutically acceptable carrier.

9. The pharmaceutical composition of claim 8, for intravenous, intramuscular, subcutaneous, transdermal, oral, nasal, parenteral or topical administration, or for administration by inhalation.

10. The pharmaceutical composition of claim 9, wherein the composition is for oral administration and formulated as a tablet, capsule, aqueous or oily solution, suspension or emulsion; or the composition is for topical administration and formulated as a cream, ointment, gel, aqueous or oil solution or suspension, salve, patch, plaster, lubricant or suppository.

11. The pharmaceutical composition of claim 8, wherein said carrier comprises a biodegradable polymer.

12. The pharmaceutical composition of claim 11, formulated for slow release of the compound.

13. The pharmaceutical composition of claim 8, wherein X is —(CR$_2$R$_2$)$_n$— wherein n is 1; R$_1$ is absent; R$_2$ is H; R$_3$ is methyl; and A is linked to position 2, 3 or 4 of the pyridine ring.

14. The pharmaceutical composition of claim 13, wherein said compound is selected from the group consisting of the oxy radical of 2-cyano-1-(1-hydroxy-2,2,6,6-tetramethylpiperidin-4-yl)-3-(pyridin-2-yl)guanidine, 2-cyano-1-(1-hydroxy-2,2,6,6-tetramethylpiperidin-4-yl)-3-(pyridin-3-yl)guanidine, and 2-cyano-1-(1-hydroxy-2,2,6,6-tetramethylpiperidin-4-yl)-3-(pyridin-4-yl)guanidine.

15. The pharmaceutical composition of claim 8, wherein X is —(CR$_2$R$_2$)$_n$— wherein n is 1; R$_1$ is F, Cl or Br, linked to position 6 of the pyridine ring; R$_2$ is H; R$_3$ is methyl; and A is linked to position 2, 3, 4 or 5 of the pyridine ring.

16. The pharmaceutical composition of claim 15, wherein said compound is selected from the group consisting of the oxy radical of 2-cyano-1-(6-fluoropyridin-2-yl)-3-(1-hydroxy-2,2,6,6-tetramethylpiperidin-4-yl)guanidine, 2-cyano-1-(6-chloropyridin-2-yl)-3-(1-hydroxy-2,2,6,6-tetramethylpiperidin-4-yl)guanidine, 2-cyano-1-(6-bromopyridin-2-yl)-3-(1-hydroxy-2,2,6,6-tetramethylpiperidin-4-yl)guanidine, 2-cyano-1-(6-fluoropyridin-3-yl)-3-(1-hydroxy-2,2,6,6-tetramethylpiperidin-4-yl)guanidine, 2-cyano-1-(6-chloropyridin-3-yl)-3-(1-hydroxy-2,2,6,6-tetramethylpiperidin-4-yl)guanidine, 2-cyano-1-(6-bromopyridin-3-yl)-3-(1-hydroxy-2,2,6,6-tetramethylpiperidin-4-yl)guanidine, 2-cyano-1-(6-fluoropyridin-4-yl)-3-(1-hydroxy-2,2,6,6-tetramethylpiperidin-4-yl)guanidine, 2-cyano-1-(6-chloropyridin-4-yl)-3-(1-hydroxy-2,2,6,6-tetramethylpiperidin-4-yl) guanidine, 2-cyano-1-(6-bromopyridin-4-yl)-3-(1-hydroxy-2,2,6,6-tetramethylpiperidin-4-yl)guanidine, 2-cyano-1-(6-fluoropyridin-5-yl)-3-(1-hydroxy-2,2,6,6-tetramethyl piperidin-4-yl)guanidine, 2-cyano-1-(6-chloropyridin-5-yl)-3-(1-hydroxy-2,2,6,6-tetramethylpiperidin-4-yl)guanidine, and 2-cyano-1-(6-bromopyridin-5-yl)-3-(1-hydroxy-2,2,6,6-tetramethylpiperidin-4-yl)guanidine.

17. The pharmaceutical composition of claim 8, wherein X is —(CR$_2$R$_2$)$_n$— wherein n is 2; R$_1$ is absent; R$_2$ is H; R$_3$ is methyl; and A is linked to position 2, 3 or 4 of the pyridine ring.

18. The pharmaceutical composition of claim 17, wherein said compound is selected from the group consisting of the oxy radical of 2-cyano-1-(1-hydroxy-2,2,7,7-tetramethylazepan-4-yl)-3-(pyridin-2-yl)guanidine, 2-cyano-1-(1-hydroxy-2,2,7,7-tetramethylazepan-4-yl)-3-(pyridin-3-yl)guanidine, and 2-cyano-1-(1-hydroxy-2,2,7,7-tetramethylazepan-4-yl)-3-(pyridin-4-yl)guanidine.

19. The pharmaceutical composition of claim 8, wherein X is —(CR$_2$R$_2$)$_n$— wherein n is 2; R$_1$ is F, Cl or Br, linked to position 6 of the pyridine ring; R$_2$ is H; R$_3$ is methyl; and A is linked to position 2, 3, 4 or 5 of the pyridine ring.

20. The pharmaceutical composition of claim 19, wherein said compound is selected from the group consisting of the oxy radical of 2-cyano-1-(6-fluoropyridin-2-yl)-3-(1-hydroxy-2,2,7,7-tetramethylazepan-4-yl)guanidine, 2-cyano-1-(6-chloropyridin-2-yl)-3-(1-hydroxy-2,2,7,7-tetramethylazepan-4-yl)guanidine, 2-cyano-1-(6-bromopyridin-2-yl)-3-(1-hydroxy-2,2,7,7-tetramethylazepan-4-yl)guanidine, 2-cyano-1-(6-fluoropyridin-3-yl)-3-(1-hydroxy-2,2,7,7-tetramethyl azepan-4-yl)guanidine, 2-cyano-1-(6-chloropyridin-3-yl)-3-(1-hydroxy-2,2,7,7-tetra methylazepan-4-yl)guanidine, 2-cyano-1-(6-bromopyridin-3-yl)-3-(1-hydroxy-2,2,7,7-tetramethylazepan-4-yl)guanidine, 2-cyano-1-(6-fluoropyridin-4-yl)-3-(1-hydroxy-2,2,7,7-tetramethylazepan-4-yl)guanidine, 2-cyano-1-(6-chloropyridin-4-yl)-3-(1-hydroxy-2,2,7,7-tetramethylazepan-4-yl)guanidine, 2-cyano-1-(6-bromopyridin-4-yl)-3-(1-hydroxy-2,2,7,7-tetramethylazepan-4-yl)guanidine, 2-cyano-1-(6-fluoropyridin-5-yl)-3-(1-hydroxy-2,2,7,7-tetramethylazepan-4-yl)guanidine, 2-cyano-1-(6-chloropyridin-5-yl)-3-(1-hydroxy-2,2,7,7-tetramethylazepan-4-yl)guanidine, and 2-cyano-1-(6-bromopyridin-5-yl)-3-(1-hydroxy-2,2,7,7-tetramethyl azepan-4-yl)guanidine.

* * * * *